(12) United States Patent
Krulevitch et al.

(10) Patent No.: US 11,607,216 B2
(45) Date of Patent: Mar. 21, 2023

(54) ADAPTIVE RESPONSES FROM SMART PACKAGING OF DRUG DELIVERY ABSORBABLE ADJUNCTS

(71) Applicant: Janssen Pharmaceuticals, Inc., Titusville, NJ (US)

(72) Inventors: Peter Krulevitch, Pleasanton, CA (US); Francesco N. Albertini, Pleasanton, CA (US); Jason L. Harris, Lebanon, OH (US); Michael J. Vendely, Lebanon, OH (US); Gregory J. Bakos, Mason, OH (US); Frederick E. Shelton, IV, Hillsboro, OH (US); Michael Hutchinson, King of Prussia, PA (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 220 days.

(21) Appl. No.: 17/068,857

(22) Filed: Oct. 13, 2020

(65) Prior Publication Data

US 2021/0346015 A1 Nov. 11, 2021

Related U.S. Application Data

(60) Provisional application No. 63/020,935, filed on May 6, 2020, provisional application No. 63/020,925, filed
(Continued)

(51) Int. Cl.
  *A61B 17/068* (2006.01)
  *A61B 17/072* (2006.01)
  *A61B 17/00* (2006.01)

(52) U.S. Cl.
  CPC ........ *A61B 17/0686* (2013.01); *A61B 17/068* (2013.01); *A61B 17/072* (2013.01);
(Continued)

(58) Field of Classification Search
  CPC ................ A61B 17/072; A61B 17/068; A61B 17/07207; A61B 17/07292; A61B 17/115;
(Continued)

(56) References Cited

U.S. PATENT DOCUMENTS 4,946,069 A   8/1990 Fuchs
5,752,965 A * 5/1998 Francis ............ A61B 17/07207
                                                606/151
(Continued)

FOREIGN PATENT DOCUMENTS

EP       3135320 A1    3/2017
WO   WO-2015187793 A1  12/2015

OTHER PUBLICATIONS

"Diet Coke and Mentos Explained," Weebly, dated no later than Mar. 16, 2020, 2 pages (available at <https://dietcoke-and-mentos.weebly.com/>).

(Continued)

*Primary Examiner* — Scott A Smith
(74) *Attorney, Agent, or Firm* — Mintz Levin Cohn Ferris Glovsky and Popeo, P.C.

(57) ABSTRACT

In general, adaptive responses from smart packaging of drug delivery absorbable adjuncts and methods of using smart packaging of drug delivery absorbable adjuncts are provided.

26 Claims, 21 Drawing Sheets

Related U.S. Application Data on May 6, 2020, provisional application No. 63/020,865, filed on May 6, 2020.

(52) U.S. Cl.
CPC .. *A61B 17/07292* (2013.01); *A61B 17/07207* (2013.01); *A61B 2017/00004* (2013.01); *A61B 2017/00084* (2013.01); *A61B 2017/00221* (2013.01); *A61B 2017/07214* (2013.01); *A61B 2017/07271* (2013.01); *A61B 2560/0271* (2013.01); *A61B 2562/029* (2013.01)

(58) Field of Classification Search
CPC .. A61B 2017/07214; A61B 2017/2919; A61B 2017/2927; A61B 2017/00017; A61B 34/20; A61B 34/30; A61B 17/0686; A61B 2017/00004; A61B 2017/00221; A61B 2017/07271
USPC ..... 227/19, 175.1, 176.1, 175.2; 606/1, 139, 606/219
See application file for complete search history.

(56) References Cited

U.S. PATENT DOCUMENTS

| | | | |
|---|---|---|---|
| 6,321,942 B1 | 11/2001 | Krampen et al. | |
| 6,939,358 B2 * | 9/2005 | Palacios | A61B 50/30 606/220 |
| 7,143,925 B2 | 12/2006 | Shelton, IV et al. | |
| 7,299,949 B2 | 11/2007 | Greiner-Perth | |
| 7,601,118 B2 | 10/2009 | Smith et al. | |
| 8,317,070 B2 | 11/2012 | Hueil et al. | |
| 8,393,514 B2 | 3/2013 | Shelton, IV et al. | |
| 8,585,659 B2 | 11/2013 | Shay | |
| 9,129,054 B2 | 9/2015 | Nawana et al. | |
| 9,314,808 B2 | 4/2016 | Allsop | |
| 9,555,950 B2 | 1/2017 | Le Maner et al. | |
| 10,251,649 B2 * | 4/2019 | Schellin | A61B 17/07292 |
| 10,456,534 B2 | 10/2019 | Reisacher et al. | |
| 10,569,071 B2 | 2/2020 | Harris et al. | |
| 10,716,564 B2 | 7/2020 | Shelton, IV et al. | |
| 11,116,505 B2 * | 9/2021 | Vendely | A61B 17/07207 |
| 11,224,423 B2 * | 1/2022 | Shelton, IV | A61B 17/072 |
| 11,291,449 B2 * | 4/2022 | Swensgard | A61B 17/068 |
| 11,406,377 B2 * | 8/2022 | Schmid | A61B 17/07207 |
| 2002/0014951 A1 | 2/2002 | Kramer et al. | |
| 2005/0070929 A1 * | 3/2005 | Dalessandro | A61B 17/07292 606/151 |
| 2007/0251835 A1 | 11/2007 | Mehta et al. | |
| 2008/0154177 A1 | 6/2008 | Moubayed et al. | |
| 2009/0206142 A1 * | 8/2009 | Huitema | A61B 17/07207 227/176.1 |
| 2012/0289979 A1 * | 11/2012 | Eskaros | A61B 17/07292 606/151 |
| 2012/0330684 A1 | 12/2012 | Jacobs et al. | |
| 2013/0146643 A1 | 6/2013 | Schmid et al. | |
| 2013/0221065 A1 | 8/2013 | Aronhalt et al. | |
| 2013/0256377 A1 | 10/2013 | Schmid et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0272575 A1 | 10/2015 | Leimbach et al. | |
| 2015/0274344 A1 | 10/2015 | Sullivan et al. | |
| 2015/0297845 A1 | 10/2015 | Shahaf et al. | |
| 2015/0351758 A1 | 12/2015 | Shelton, IV et al. | |
| 2017/0119391 A1 | 5/2017 | Schellin et al. | |
| 2017/0296213 A1 | 10/2017 | Swensgard et al. | |
| 2018/0060527 A1 | 3/2018 | Kalyanpur et al. | |
| 2018/0189638 A1 | 7/2018 | Nurvitadhi et al. | |
| 2018/0361085 A1 | 12/2018 | Malhotra et al. | |
| 2019/0200844 A1 | 7/2019 | Shelton, IV et al. | |
| 2019/0200981 A1 | 7/2019 | Harris et al. | |
| 2019/0201046 A1 | 7/2019 | Shelton, IV et al. | |
| 2019/0201114 A1 | 7/2019 | Shelton, IV et al. | |
| 2019/0201140 A1 | 7/2019 | Yates et al. | |
| 2019/0206004 A1 | 7/2019 | Shelton, IV et al. | |
| 2019/0206555 A1 | 7/2019 | Morgan et al. | |
| 2019/0207857 A1 | 7/2019 | Shelton, IV et al. | |

OTHER PUBLICATIONS

"Dual Component Epoxy Cartridges K-Series Syringe," Adhesive Dispensing Ltd., dated no later than Mar. 21, 2020, 2 pages (available at <https://www.adhesivedispensing.net/Dual_Component_K_Series_Dispensing_s/236.htm>).

"Molecular Sieve vs Silica Gel: What's the Difference?", Multisorb Fixation Group, dated no later than Mar. 24, 2020, 2 pages (available at <https://www.multisorb.com/blog/pharmaceuticals/molecular-sieve-vs-silica-gel-whats-the-difference/>).

"Orbeez® Toys—Add Water to Make Them Grow!", Maya Toys, dated no later than Mar. 24, 2020, 2 pages (available at <https://mayatoys.net/pages/orbeez>).

"Philips Medication Dispenser," Philips Lifeline, dated no later than Mar. 17, 2020, 6 pages (available at <https://www.lifeline.philips.com/pill-dispenser/health-mdp.html>).

"Study Shows High Altitude and Medication May Not Mix," healthNEWS, University of Cincinnati Academic Health Center, Jan. 14, 1999, 1 page (available at <http://healthnews.uc.edu/news/?/153/>).

"The Companion Dual Chamber Reconstitution Syringe," Credence MedSystems, Inc, dated no later than Mar. 18, 2020, 3 pages <available at <https://www.credencemed.com/dual-chamber/>).

"VapourSoft® Technology," Bespak Europe Ltd., dated no later than Mar. 16, 2020, 2 pages (available at <https://bespak.com/products/injection-devices/vapoursoft-technology/>).

Jae Hung Park et al., "Biodegradable Polymers for Microencapsulation of Drugs," Molecules 2005, 10, p. 146-161.

Man Chiu Fung, "Experimental and numerical study of spray characteristics of nasal spray devices," School of Aerospace, Mechanical and Manufacturing Engineering Science, Engineering and Technology Portfolio, RMIT University, Aug. 2013 (179 pages).

Rafi, "14 List of Chemicals That Glow Under Black Light—Application," Jan. 24, 2018, 3 pages (available at <https://azchemistry.com/list-of-chemicals-that-glow-under-black-light>).

International Search Report and Written Opinion for Intl. App. No. PCT/IB2021/058429 dated Jan. 24, 2022.

* cited by examiner

ADAPTIVE RESPONSES FROM SMART PACKAGING OF DRUG DELIVERY ABSORBABLE ADJUNCTS

CROSS REFERENCE TO RELATED APPLICATIONS

The present application claims priority to U.S. Prov. App. No. 63/020,865 entitled "Drug Delivery Systems And Methods" filed May 6, 2020, U.S. Prov. App. No. 63/020,925 entitled "Remote Aggregation Of Data For Drug Administration Devices" filed May 6, 2020, and U.S. Prov. App. No. 63/020,935 entitled "Drug Administration Device And System For Establishing A Dosage Regimen And Compatibility Of Components" filed May 6, 2020, which are hereby incorporated by reference in their entireties.

FIELD

The present disclosure relates generally to adaptive responses from smart packaging of drug delivery absorbable adjuncts and methods of using smart packaging of drug delivery absorbable adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

It can be beneficial to apply adjuncts to tissue at the surgical site. For example, leaks can occur due to holes and/or tears in tissue formed by staples when penetrating the tissue, and adjuncts can be used to prevent blood, air, gastrointestinal fluids, and/or other fluids from seeping through the holes formed by the staples. For another example, the adjunct can include a medicant therein that is configured to be released from the adjunct after the adjunct has been applied to tissue. The medicant can be configured to provide one or more benefits for healing, such as encouraging hemostasis, reducing inflammation, and stimulate cell proliferation.

Adjuncts can be absorbable. An adjunct being absorbable allows the adjunct to dissolve or degrade within a patient's body and thus not require additional surgery or other process to remove the adjunct from the patient's body. In instances in which the adjunct contains a medicant, the adjunct being absorbable facilitates automatic release of the medicant from the adjunct as the adjunct dissolves or degrades. However, medicants and/or material forming absorbable adjuncts can be adversely affected by any of a variety of factors between the adjunct being packaged and the adjunct being used. For example, environmental factors may cause a reduction in the medicant's effectiveness and/or may cause the adjunct to begin degrading before being implanted in a patient's body. For another example, a medicant may expire before the adjunct containing the medicant is implanted in a patient's body.

Accordingly, there remains a need for improved adjuncts.

SUMMARY

In general, adaptive responses from smart packaging of drug delivery absorbable adjuncts and methods of using smart packaging of drug delivery absorbable adjuncts are provided.

In one aspect, a surgical system is provided that in one embodiment includes a bioabsorbable adjunct configured to be implanted in a body of a patient, a drug configured to be releasably retained by the adjunct, and a sensor configured to monitor at least one exposure condition of at least one of the adjunct and the drug prior to the adjunct being implanted in the body of the patient. With the adjunct implanted in the body of the patient and the drug releasably retained by the adjunct, the drug is configured to be released from the adjunct into the body of the patient. The at least one exposure condition is a condition that affects performance of at least one of the adjunct in the body of the patient and the drug in the body of the patient.

The surgical system can have any number of variations. For example, the surgical system can also include a staple cartridge to which the adjunct is releasably coupled, and the drug can be releasably retained by the adjunct. In at least some embodiments, the staple cartridge can be a standalone element configured to be removably and replaceably seated in an end effector of a surgical stapler, the staple cartridge can be seated in an end effector of a surgical stapler, and/or the sensor can be attached to the staple cartridge.

For another example, the at least one exposure condition can include at least one of temperature, humidity, time, ultraviolet, oxygen, and light. For yet another example, the at least one exposure condition can include at least one of humidity and oxygen, humidity and oxygen affecting structural resilience of the adjunct. For another example, the at least one exposure condition can include at least time, time affecting an expiration date of the drug. For still another example, the at least one exposure condition can include at least one of light, ultraviolet, and temperature, light, ultraviolet, and temperature each affecting a viability of the drug.

For yet another example, the surgical system can also include a communications interface configured to communicate data gathered by the sensor to a processor. In at least some embodiments, the processor can be local to the adjunct and can be configured to cause the data to be communicated to a remote cloud server, the processor can be remote from the adjunct, and/or the processor can be configured to analyze the data and thereby determine whether at least one exposure condition adversely affected performance of the at least one of the adjunct and the drug and, in at least some embodiments, the processor can be configured to cause a warning to be provided to a user in response to determining that the at least one exposure condition adversely affected performance of the at least one of the adjunct and the drug.

For another example, the surgical system can include a packaging unit in which the adjunct and the drug are disposed, and the sensor can be attached to the packaging unit. For yet another example, the surgical system can include a second sensor configured to monitor at least one exposure condition of the drug from an initial time before the drug is retained by the adjunct to a second time in which the drug is retained by the adjunct.

In another aspect, a drug monitoring method is provided that in one embodiment includes monitoring, by a sensor, at least one exposure condition of a drug retained in a bioabsorbable adjunct configured to be implanted in a body of a patient after the monitoring, transmitting data representative of the at least one exposure condition to a communications interface in communication with the sensor, receiving and transmitting, by the communications interface, the data to a processor that is in communication with the communications interface, and determining, by the processor, viability of the drug based on the received data characterizing the at least one exposure condition. The drug monitoring method can have any number of variations.

In another aspect, a method of establishing compatibility of surgical components is provided that in one embodiment includes acquiring first component data relating to at least one of a surgical stapler, a staple cartridge containing a plurality of surgical staples, a bioabsorbable adjunct releasably coupled to the staple cartridge, and a drug retained releasably retained by the adjunct, comparing the first component data with acceptable first component data, and setting an operational status of the stapler based on the comparison of the first component data with acceptable first component data.

The method of establishing compatibility of surgical components can vary in any number of ways. For example, acquiring the first component data can include communicating the first component data from the first component to an external device that is external to the stapler. For another example, acquiring the first component data can be carried out on an external device that is external to the stapler. For yet another example, acquiring the first component data can include communicating the first component data from the first component to a processor of the stapler. For still another example, comparing the first component data with acceptable first component data can occur on an external device that is external to the stapler. For another example, comparing the first component data with acceptable first component data can utilize a processor of the stapler. For still another example, the first component data can include image data, and acquiring the first component data can include imaging the at least one of the surgical stapler, the staple cartridge, the adjunct, and the drug. For yet another example, the first component data can be on the at least one of the surgical stapler, the staple cartridge, the adjunct, and a drug holder holding the drug therein. For still another example, the first component data can be on a packaging unit packaging at least one of the at least one of the surgical stapler, the staple cartridge, the adjunct, and the drug. For another example, setting the operational status of the stapler can include one of (1) flagging that the operational status should be fully operational when the first component data corresponds with acceptable first component data, and flagging that the operational status should not be fully operational when the first component data does not correspond with acceptable first component data, and (2) setting the operational status as fully operational when all required flags indicate that the operational status should be fully operational, and setting the operational status as not fully operational when any required flags indicate the operational status should not be fully operational.

In another aspect, a surgical system is provided that in one embodiment includes a bioabsorbable adjunct configured to be implanted in a body of a patient, a drug configured to be releasably retained by the adjunct, a staple cartridge to which the adjunct is releasably coupled, data storage configured to contain first component data regarding at least one of the adjunct, the drug, and the staple cartridge, and a processor configured to receive and compare the first component data with acceptable first component data and set an operational status of a surgical stapler based on the comparison. With the adjunct implanted in the body of the patient and the drug releasably retained by the adjunct, the drug is configured to be released from the adjunct into the body of the patient.

The surgical system can vary in any number of ways. For example, the surgical system can also include the surgical stapler.

BRIEF DESCRIPTION OF DRAWINGS

The present invention is described by way of reference to the accompanying figures which are as follows.

DETAILED DESCRIPTION

Figure 1:
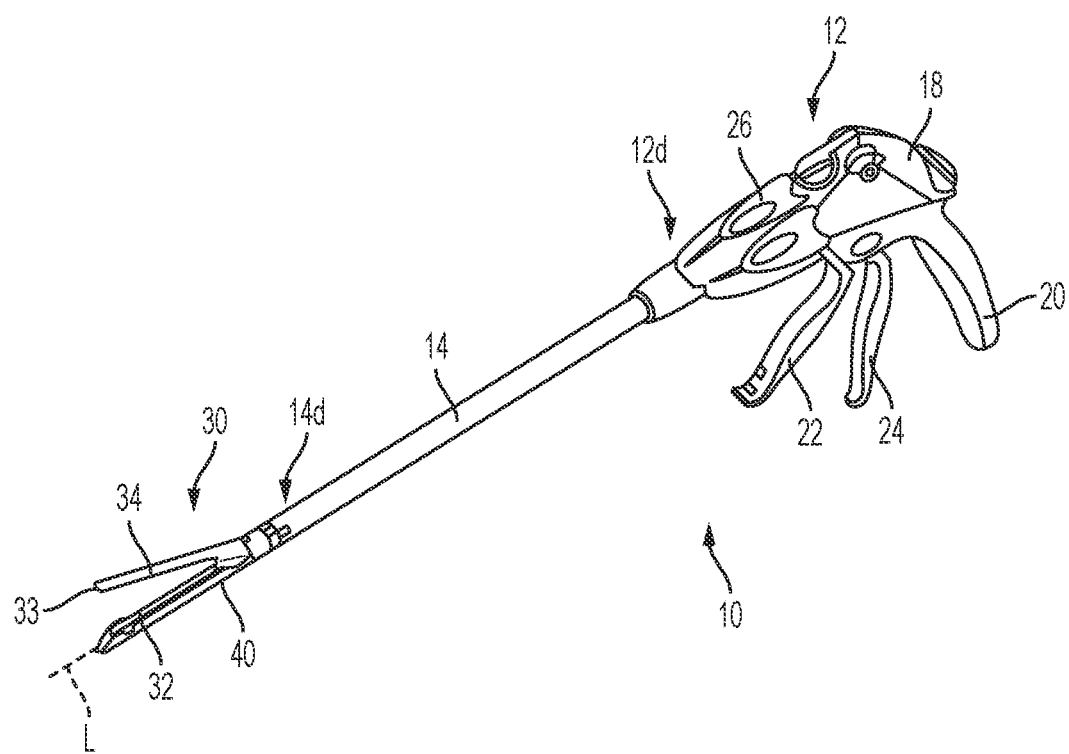
FIG. 1 is a perspective view of one embodiment of a linear surgical stapler.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

The adjunct(s) can also have medicant(s) thereon and/or therein. "Medicants" are also referred to herein as "drugs." The medicant(s) can vary depending on the desired effect of the medicant(s) on the surrounding tissue. For example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc.

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler is configured to create longitudinal staple lines and includes elongate jaws with a cartridge coupled thereto containing longitudinal staple rows. The linear stapler can include a knife or other cutting element capable of creating a cut between the staple rows along tissue held within the jaws. In general, a circular stapler is configured to create annular staple lines and includes circular jaws with a cartridge containing annular staple rows. The circular stapler can include a knife or other cutting element capable of creating a cut inside of the rows of staples to define an opening through tissue held within the jaws. The staplers, whether linear or circular, can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjuncts and one or more medicants. The stapler 10 includes a handle assembly 12, a shaft 14 extending distally from a distal end 12d of the handle assembly 12, and an end effector 30 at a distal end 14d of the shaft 14. The end effector 30 includes opposed lower and upper jaws 32, 34, although other types of end effectors can be used with the shaft 14, the handle assembly 12, and components associated with the same. The lower jaw 32 includes a staple channel 56 configured to support a staple cartridge 40, and the upper jaw 34 includes an anvil surface 33 that faces the lower jaw 32 and that is configured to operate as an anvil to help deploy staples of the staple cartridge 40 (the staples are obscured in FIG. 1 and FIG. 2). At least one of the opposed lower and upper jaws 32, 34 is moveable relative to the other of the lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system are configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. The handle assembly 12 includes a rotation knob 26 mounted adjacent a distal end 12d thereof configured to be actuated, e.g., rotated, to cause rotation of the shaft 14 and/or the end effector 30 with respect to the handle assembly 12 about a longitudinal axis L of the shaft 14. The handle assembly 12 also includes clamping components, as part of a clamping system configured to be actuated by a clamping trigger 22, and firing components, as part of a firing system configured to be actuated by a firing trigger 24. The clamping and firing triggers 22, 24 can be biased to an open position with respect to a stationary handle 20, for instance by a torsion spring. Movement of the clamping trigger 22 toward the stationary handle 20 is configured to actuate the clamping system, described below, to cause the jaws 32, 34 to collapse towards each other and to thereby clamp tissue therebetween. Movement of the firing trigger 24 is configured to actuate the firing system, described below, to cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
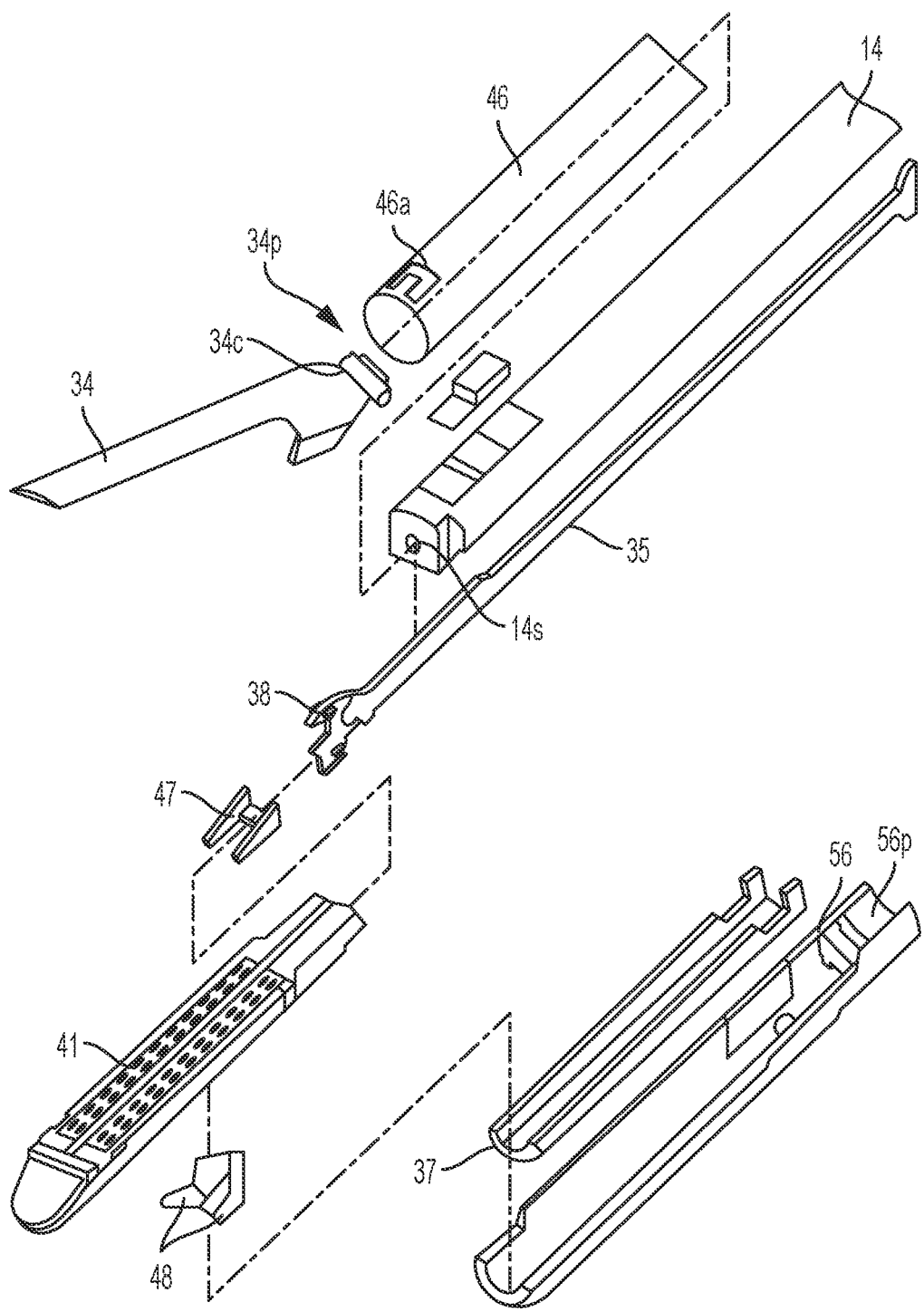
FIG. 2 is an exploded view of a distal portion of the stapler of FIG. 1.

As shown in FIG. 2, the end effector 30 of the illustrated implementation includes the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 includes a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation a proximal pivoting end 34p of the upper jaw 34 is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

The staple cartridge 40 can be fixed in the lower jaw 32 so as to not be removable therefrom. In other implementations, the staple cartridge 40 is configured to be removably and replaceably seated in the lower jaw 32. The staple cartridge 40 being removable and replaceable allows the stapler 10 to be used to fire staples from a plurality of cartridges and for a surgeon or other medical professional to choose a particular cartridge and staples as desired for the particular surgical procedure being performed, the particular tissue being stapled, and/or the particular patient's anatomy.

Various clamping components can be used to effect opening and closing of the jaws 32, 34 to selectively clamp tissue therebetween. As illustrated in this example, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 can be effected by relative motion of the lower jaw 32 with respect to the upper jaw 34, relative motion of the upper jaw 34 with respect to the lower jaw 32, or by motion of both jaws 32, 34 with respect to one another.

Figure 3:
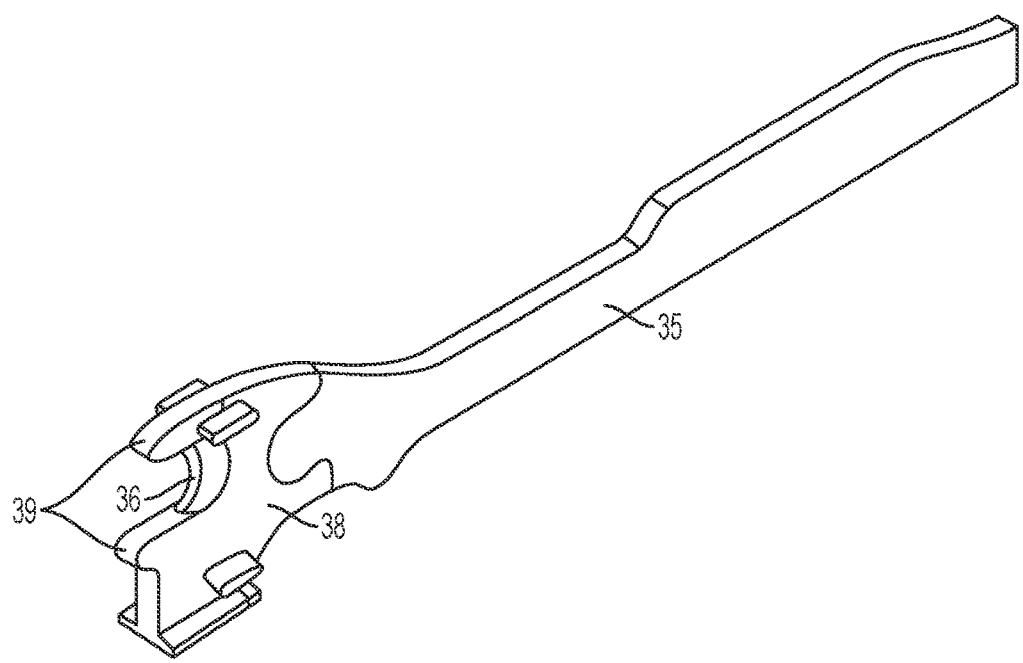
FIG. 3 is a perspective view of a firing bar of the stapler of FIG. 1.

The firing components of the illustrated implementation includes a firing bar 35, as shown in FIG. 3, having an E-beam 38 on a distal end thereof. The firing bar 35 is disposed within the shaft 14, for example in a longitudinal firing bar slot 14s of the shaft 14, and is guided by a firing motion from the handle 12. Actuation of the firing trigger 24 is configured to affect distal motion of the E-beam 38 through at least a portion of the end effector 30 to thereby cause the firing of staples contained within the staple cartridge 40. As illustrated, guides 39 projecting from a distal end of the E-Beam 38 are configured to engage a wedge sled 47 shown in FIG. 2, which in turn is configured to push staple drivers 48 upwardly through staple cavities 41 formed in the staple cartridge 40. Upward movement of the staple drivers 48 is configured to apply an upward force on each of the plurality of staples within the cartridge 40 to thereby push the staples upwardly against the anvil surface 33 of the upper jaw 34 and create formed staples.

In addition to causing the firing of staples, the E-beam 38 is configured to facilitate closure of the jaws 32, 34, spacing of the upper jaw 34 from the staple cartridge 40, and/or severing of tissue captured between the jaws 32, 34. In particular, a pair of top pins and a pair of bottom pins are configured to engage one or both of the upper and lower jaws 32, 34 to compress the jaws 32, 34 toward one another as the firing bar 35 advances through the end effector 30. Simultaneously, the knife 36 extending between the top and bottom pins is configured to sever tissue captured between the jaws 32, 34.

In use, the surgical stapler 10 is configured to be disposed in a cannula or port and disposed at a surgical site. A tissue to be cut and stapled is positioned between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 is pulled toward the stationary handle 20 to actuate the clamping system. The actuation of the clamping trigger 22 causes components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 is pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
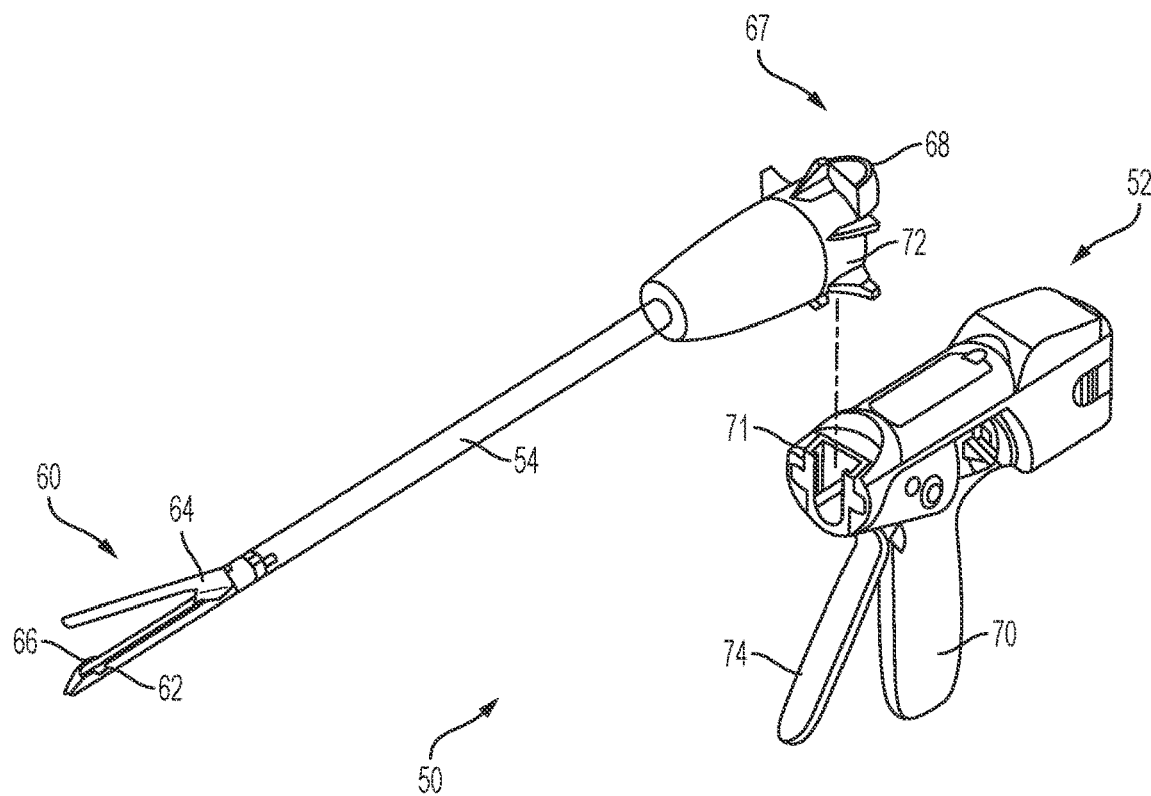
FIG. 4 is a perspective view of another embodiment of a linear surgical stapler.

Another example of a surgical instrument in the form of a linear surgical stapler 50 is illustrated in FIG. 4. The stapler 50 is generally be configured and used similar to the stapler 10 of FIG. 1. Similar to the surgical instrument 10 of FIG. 1, the surgical instrument 50 of FIG. 4 includes a handle assembly 52 with a shaft 54 extending distally therefrom and an end effector 60 on a distal end of the shaft 54 for treating tissue. Upper and lower jaws 64, 62 of the end effector 60 are configured to capture tissue therebetween, to staple the tissue by firing of staples from a cartridge 66 disposed in the lower jaw 62, and/or to create an incision in the tissue. In this implementation, an attachment portion 67 on a proximal end of the shaft 54 is configured to allow for removable attachment of the shaft 54 and the end effector 60 to the handle assembly 52. In particular, mating features 68 of the attachment portion 67 are configured to mate to complementary mating features 71 of the handle assembly 52. The mating features 68, 71 are configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 is configured to allow for detachment of only a distal portion of the shaft 54. Detachable coupling of the shaft 54 and/or the end effector 60 may allow for selective attachment of a desired end effector 60 for a particular procedure, and/or for reuse of the handle assembly 52 for multiple different procedures.

The handle assembly 52 can have one or more features thereon to manipulate and operate the end effector 60. In this illustrated example, a rotation knob 72 is mounted on a distal end of the handle assembly 52 is configured to be actuated, e.g., rotated, to cause rotation of the shaft 54 and/or the end effector 60 with respect to the handle assembly 52. The handle assembly 52 includes clamping components, as part of a clamping system actuated by a movable trigger 74, and firing components, as part of a firing system that is also actuated by the movable trigger 74. Movement of the movable trigger 74 toward a stationary handle 70 through a first range of motion is configured to actuate the clamping components to cause the opposed jaws 62, 64 to approximate toward one another to a closed position. In some implementations, only one of the opposed jaws 62, 24 can move to the jaws 62, 64 to the closed position. Further movement of the movable trigger 74 toward the stationary handle 70 through a second range of motion is configured to actuate firing components to cause the ejection of the staples from the staple cartridge 66 and/or the advancement of a knife or other cutting element (not shown) to sever tissue captured between the jaws 62, 64.

Figure 5:
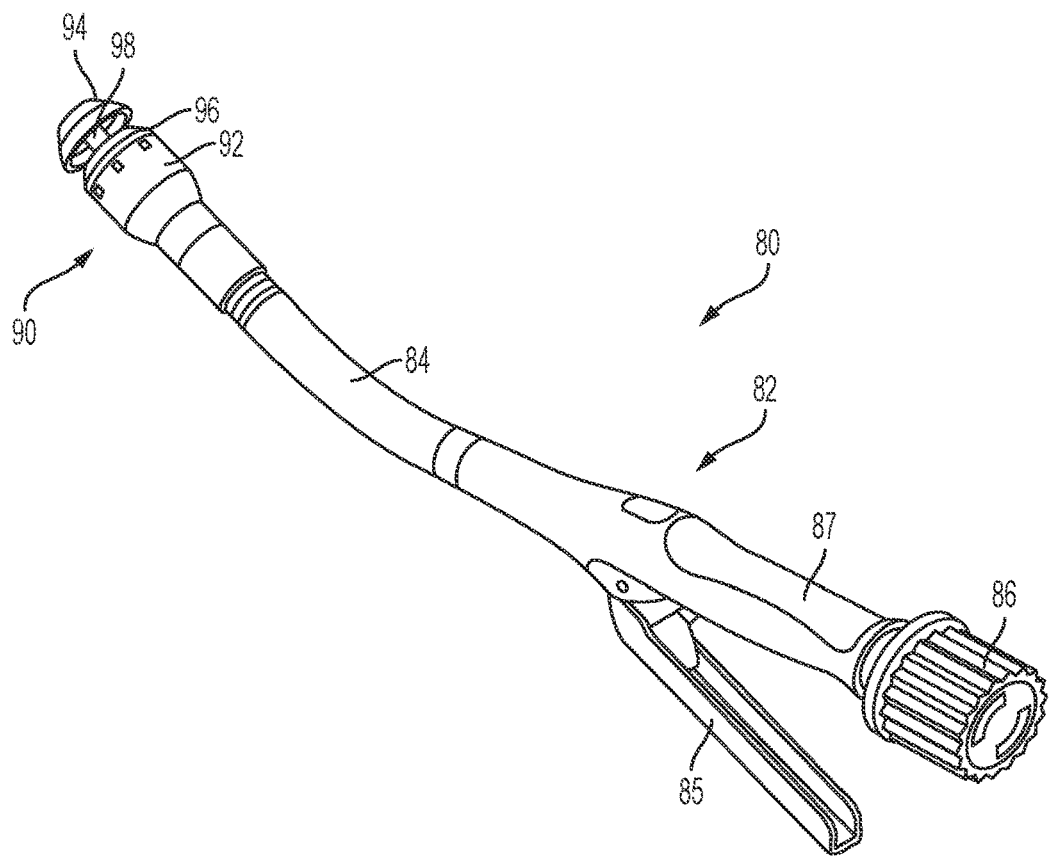
FIG. 5 is a perspective view of one embodiment of a circular surgical stapler.

One example of a surgical instrument in the form of a circular surgical stapler 80 is illustrated in FIG. 5. The circular stapler 80 is generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and an end effector 90 on a distal end of the shaft 84. The end effector 90 includes a cartridge assembly 92 and an anvil 94, each with a tissue-contacting surface that is substantially circular in shape. The cartridge assembly 92 and the anvil 94 are coupled together via a shaft 98 extending from the anvil 94 to the handle assembly 82 of the stapler 80. Manipulating an actuator 85 on the handle assembly 82 is configured to retract and advance the shaft 98 to move the anvil 94 relative to the cartridge assembly 92. The anvil 94 and cartridge assembly 92 are configured to capture tissue therebetween, staple the tissue by firing of staples from a cartridge 96 of the cartridge assembly 92, and/or create an incision in the tissue. In general, the cartridge assembly 92 houses a cartridge containing the staples and deploys staples therefrom against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 84 can be disposed within the cartridge assembly 92 and extend distally outside of the cartridge assembly 92, terminating in a distal mating feature. The second portion of the shaft 84 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. In this example, the handle assembly 82 includes a rotation knob 86 disposed thereon configured to be actuated, e.g., rotated, to facilitate positioning of the end effector 90 via rotation of the end effector 90, and includes the trigger 85 configured to be actuated to actuate functions of the end effector 90. Movement of the trigger 85 toward a stationary handle 87 through a first range of motion is configured to actuate components of the stapler's clamping system to approximate the jaws 62, 64, e.g., to move the anvil 94 toward the cartridge assembly 92. Movement of the trigger 85 toward the stationary handle 87 through a second range of motion is configured to actuate components of the stapler's firing system to cause the staples to deploy from the staple cartridge assembly 92 and/or to cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" filed Feb. 8, 2013, U.S. Pat. No. 8,393,514 entitled "Selectively Orientable Implantable Fastener Cartridge" filed Sep. 30, 2010, U.S. Pat. No. 8,317,070 entitled "Surgical Stapling Devices That Produce Formed Staples Having Different Lengths" filed Feb. 28, 2007, U.S. Pat. No. 7,143,925 entitled "Surgical Instrument Incorporating EAP Blocking Lockout Mechanism" filed Jun. 21, 2005, U.S. Pat. Pub. No. 2015/0134077 entitled "Sealing Materials For Use In Surgical Stapling" filed Nov. 8, 2013, U.S. Pat. Pub. No. 2015/0134076, entitled "Hybrid Adjunct Materials for Use in Surgical Stapling" filed on Nov. 8, 2013, U.S. Pat. Pub. No. 2015/0133996 entitled "Positively Charged Implantable Materials and Method of Forming the Same" filed on Nov. 8, 2013, U.S. Pat. Pub. No. 2015/0129634 entitled "Tissue Ingrowth Materials and Method of Using the Same" filed on Nov. 8, 2013, U.S. Pat. Pub. No. 2015/0133995 entitled "Hybrid Adjunct Materials for Use in Surgical Stapling" filed on Nov. 8, 2013, U.S. Pat. Pub. No. 2015/0272575 entitled "Surgical Instrument Comprising a Sensor System" and filed on Mar. 26, 2014, and U.S. Pat. Pub. No. 2015/0351758 entitled "Adjunct Materials and Methods of Using Same in Surgical Methods for Tissue Sealing" filed on Jun. 10, 2014, which are hereby incorporated by reference herein in their entireties.

Adjuncts as described herein are configured for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010.

An adjunct can be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" filed Feb. 8, 2013, which is hereby incorporated by reference in its entirety. The adjunct can be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" filed Feb. 8, 2013, and in U.S. Pat. No. 7,601,118 entitled "Minimally Invasive Medical Implant And Insertion Device And Method For Using The Same" filed Sep. 12, 2007, which are hereby incorporated by reference in their entireties.

The adjuncts described herein can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

In an exemplary embodiment, the adjunct is bioabsorbable and biocompatible. The materials forming adjuncts can include bioabsorbable and biocompatible polymers, including homopolymers and copolymers. Examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl®, Vicryl Rapide™, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly(lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima).

An adjunct can also include active agents, such as active cell culture (e.g., diced autologous tissue, agents used for stem cell therapy (e.g., Biosutures and Cellerix S.L.), hemostatic agents, and tissue healing agents. Examples of hemostatic agents include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. Examples of medicants include antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+, Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). Examples of the growth factors further include erythropoietin (e.g., Darbepoetin, Epocept, Dynepo, Epomax, NeoRecormon, Silapo, and Retacrit).

Examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Examples of anesthetics include local anesthetics (e.g., Lidocaine, Benzocaine, and Ropivacaine) and general anesthetic.

Examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids gents that inhibit mitosis and microtubule formation (e.g., Vinblastine, Vincristine, Vindesine, Vinorelbine), anti-ileus agents, pro-motility agents, immunosuppressants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, examples of which include Hyaluronic acid/Carboxymethyl cellulose (seprafilm), Oxidized Regenerated Cellulose (Interceed), and Icodextrin 4% (Extraneal, Adept).

An adjunct can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Various exemplary examples of adjuncts and use thereof are further described in U.S. Pat. No. 10,569,071 entitled "Medicant Eluting Adjuncts And Methods Of Using Medicant Eluting Adjuncts" issued Feb. 25, 2020, which is hereby incorporated by reference in its entirety.

Figure 6:
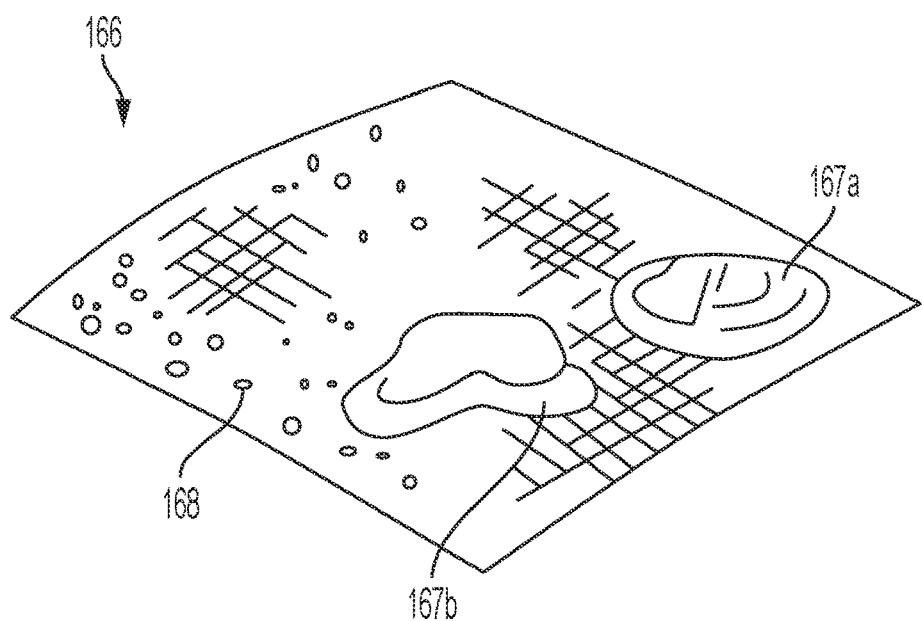
FIG. 6 is a perspective view of one embodiment of an adjunct.
Figure 7:
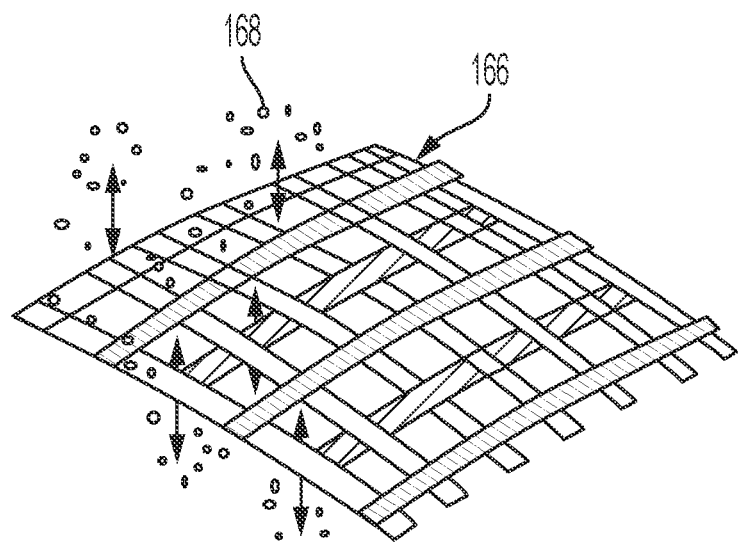
FIG. 7 is a perspective view of a portion of the adjunct of FIG. 6 releasing medicant therefrom.

FIGS. 6 and 7 illustrate one example of an adjunct 166 having a medicant 168 releasably retained therein. In this example, the adjunct 166 is in the form of a sheet-like fiber woven mesh. As shown in FIG. 6, the tight fibers of the adjunct 166 in its original configuration allow the medicant 168 to be retained therein. When the adjunct 166 is delivered at the treatment site, water and/or other agents, shown schematically as drops 167a, 167b in FIG. 6, are configured to cause the fibers to swell and elongate such that the distances between the fibers increase, as shown in FIG. 7. In this way, the medicant 168 is released, as also shown in FIG. 7. A person skilled in the art will appreciate that the adjunct 166 can be formed from different types of fibers. The fibers can have different absorption rates, density, direction, patterns, size, and other properties that are selected so as to provide desired tissue re-growth. While some regions of the adjunct can be configured to release at least one medicant so as to encourage tissue re-growth, one or more regions of the adjunct can be configured to release at least one medicant so as to discourage tissue re-growth.

Figure 8:
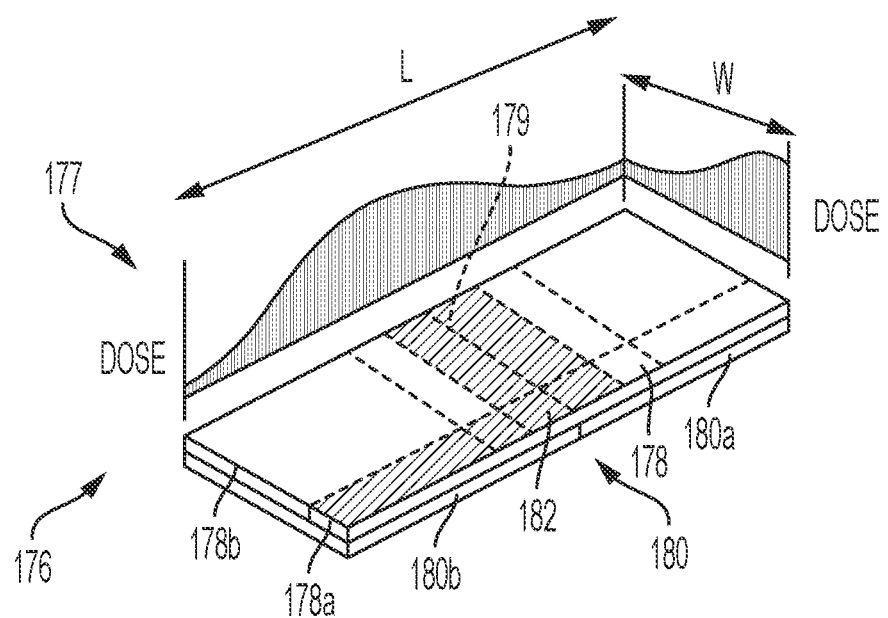
FIG. 8 is a perspective view of another embodiment of an adjunct.

FIG. 8 illustrates as example of an adjunct 176 in the form of a laminate including heterogeneous portions or layers having different degradation rates and incorporating different medicants. As shown, the adjunct 176 includes a top layer or portion 178 and a bottom layer or portion 180 that have different degradation rates. Furthermore, each of the top and bottom portions 178, 180 can have various portions having degradation rates that vary in a distinct or continuous manner. The degradation rates can vary across the adjunct in a number of suitable ways that depend on a desired treatment effect to be provided by the adjunct.

In the example of FIG. 8, the top portion 178 of the adjunct 176 includes two portions 178a, 178b having different degradation rates. The bottom portion 180 includes two portions 180a, 180b having different degradation rates. Each of the portions can include a different medicant such that, as a portion degrades, a respective medicant is eluted or released. The degradation rates and distribution of the medicants within one or more of the portions 178a, 178b, 180a, 180b can further vary in a distinct or continuous manner such that the adjunct 176 can provide an elution profile shown in a graph 177 in FIG. 8. As shown, a central area 182 of the adjunct 176 centered around a mid-portion 179 thereof has an increased elution rate of one or more medicants that peaks at the mid-portion 179, whereas smaller amount of the medicant(s) is eluted from opposite sides of the adjunct 176 along its length L. The increased elution rate can be due to properties of the adjunct 176 at the central area 182 and the concentration of the medicants.

As also shown in FIG. 8, the adjunct 176 is configured to release medicants in different elution profiles along the length L thereof and along a width W thereof. For example, the medicants can be released along the width W as a bolus dose and along the length as a time-release dose. Release of one or more of the medicants can regulate release of at least one other of the medicants. However, the medicants can be released in any other manner, depending on a desired treatment to be delivered.

Figure 9:
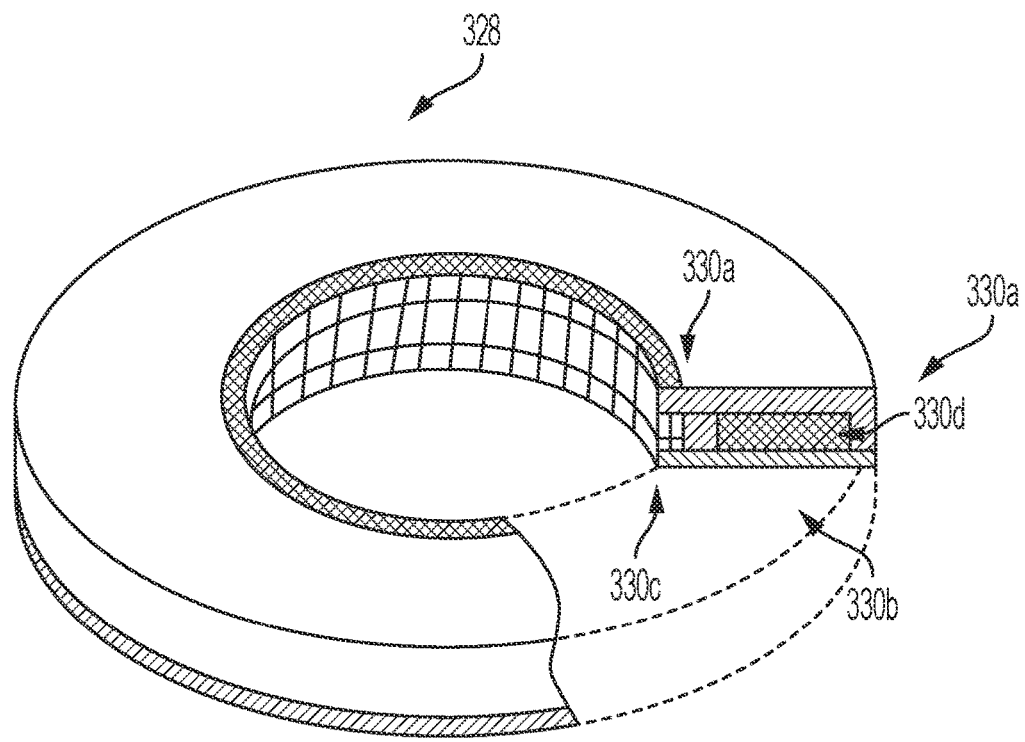
FIG. 9 is a perspective view of yet another embodiment of an adjunct.

The adjunct 176 has a generally rectangular shape to facilitate its use thereof with a linear stapler. Other adjuncts can have a different shape to facilitate use thereof with a circular stapler. FIG. 9 illustrates such an implementation of an adjunct 328 configured for use with a circular surgical stapler. The adjunct 328 thus has a generally circular shape.

The adjunct 328 in the illustrated implementation of FIG. 9 is formed from a plurality of fibers and includes a plurality of heterogeneous fiber lattice sections 330a, 330b, 330c, 330d. The first fiber lattice section 330a is located on a top side and on an exterior side of the adjunct 328 and is configured to discourage tissue growth by having a first medicant (not shown) releasably retained therein that is configured to discourage tissue growth, such as an anti-adhesion agent. The second fiber lattice section 330b is located on a bottom side of the adjunct 328 and is configured to encourage tissue growth by having a second medicant (not shown) releasably retained therein that is configured to encourage tissue growth, such as a growth factor. The third fiber lattice section 330c is located on an interior side of the adjunct 328 and is configured to facilitate hemostasis by having a third medicant 320 releasably retained therein that is configured to facilitate hemostasis, such as a hemostatic agent. The fourth fiber lattice section 330d is located in an interior area of the adjunct 328 and is configured to space apart the top and bottom sides of the adjunct 328 to thereby space apart the tissue growth-encouraging and tissue growth-discouraging portions of the adjunct 328. The fourth fiber lattice section 330d can have a fourth medicant (not shown) releasably retained therein. The fourth medicant can include, for example, an anti-adhesion agent or can include ORC and/or another hemostatic agent.

Figure 10:
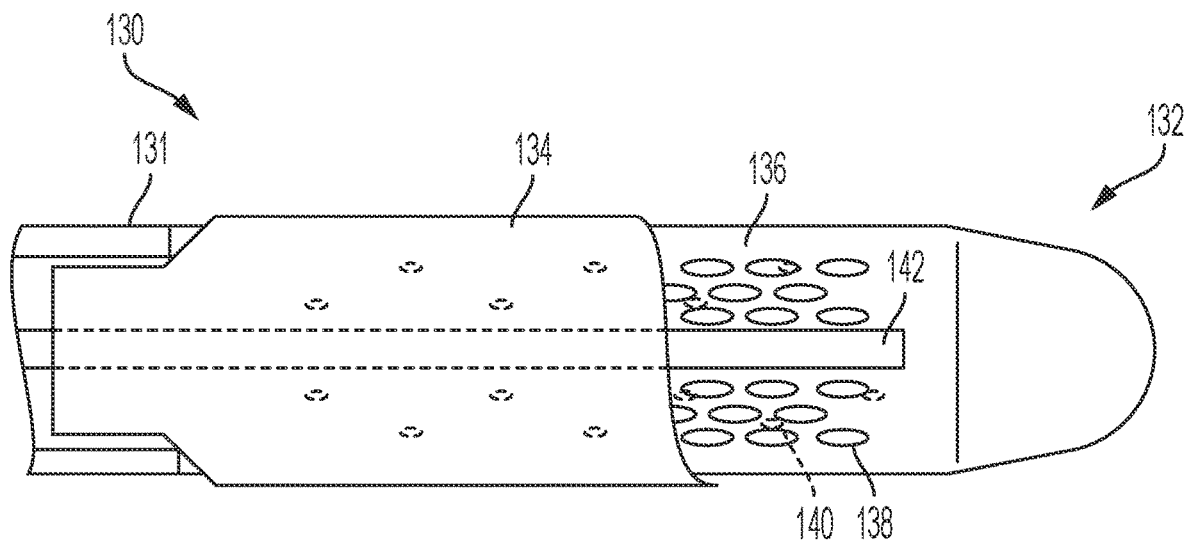
FIG. 10 is a top view of a portion of a surgical stapler with an adjunct releasably coupled to a staple cartridge.

FIG. 10 illustrates an example of an adjunct 134 releasably coupled to a staple cartridge 132 of a linear stapler. FIG. 10 illustrates a portion of a lower jaw 131 of the stapler's end effector 130. The lower jaw 131 has a cartridge 132 disposed therein, similar to the staple cartridge 40 discussed above, that includes a tissue-facing surface 136 with the adjunct 134 disposed thereon. Only a portion of the adjunct 134 is shown for clarity of illustration of the end effector 130.

The adjunct 134 can be releasably coupled to the cartridge 132 in any of a variety of ways. In this example, the cartridge 132 includes one or more connection cavities 140 extending between and connecting staple cavities 138 of the cartridge 132. The connection cavities 140 are in the form of recesses or bores in this example but can have a variety of configurations and shapes. For example, the connection cavities 140 can be generally oval in shape and smaller than the staple cavities 138. In other embodiments, the cavities can be generally circular, generally square, generally rectangular, etc., and they can be larger than, equal in size to, or a combination of sizes relative to the staple cavities 138. The connection cavities 140 can be disposed between rows of the staple cavities 138. However, the connection cavities 140 can have any number of configurations, such as each staple cavity 138 having a connection cavity 140 adjacent thereto. While the connection cavities 140 are formed adjacent to the staple cavities 138 on the tissue-facing surface 136, they can be formed elsewhere. For example, the cavities 138 can be formed at the interface of the cartridge and a staple tray such that some portion of the inner surface of the cavity is a surface of the cartridge, and another portion is a surface of the tray. Furthermore, connection cavities for attaching and detaching an adjunct need not be limited to the tissue-facing surface of the cartridge. For example, connection cavities can be formed along the edge of the tissue-facing surface of the cartridge such that when the end effector is assembled, a portion of the connection cavity will be formed by a staple tray. Alternatively, rather than connection cavities, a channel can be formed between the tissue-facing surfaces of the cartridge and the tray. Portions of the adjunct can be tucked into the channel, or adhered to the tissue-facing surface at locations proximal to the channel, during manufacturing or at any time prior to use. In such an embodiment, drivers near the outermost edge of the tissue-facing surface of the cartridge can have an adjunct releasing mechanism such that portions of the adjunct are pushed out of the channel, and/or break the adhesive bond along the channel between the adjunct and the cartridge during firing.

The adjunct 134 includes protrusions or tabs disposed on a surface that contacts the tissue-facing surface 136, and the protrusions are configured to extend into and engage with the connection cavities 140. The adjunct 134 can be configured to engage the tissue-facing surface 136 through a variety of means. For instance, protrusions on the adjunct can be received in the connection cavities and securely attaching due to a friction fit attachment. In such an example, an adjunct can be created by extruding a film such that it has protrusions in predefined locations that correspond to locations of the connection cavities on a tissue-facing surface of a cartridge. In other embodiments, the adjunct can be made from a Vicryl® (polyglactin 910) material, and can include one or more backing layers made of polydioxanone (PDS). The one or more PDS layers can be fused to the Vicryl® material, and the one or more PDS layers can include protrusions that can be configured to extend into and mate with the connection cavities. In addition or alternatively, the adjunct can engage the tissue-facing surface through use of an adhesive, such as cyanoacrylate.

As staple drivers move relative to the cartridge 132, the staple drivers are configured to move upward through the staple cavities 138 to apply an upward force on each of the plurality of staples within the cartridge 132. The staple drivers can include an adjunct releasing mechanism, such as a post or other element, configured to be received in the connection cavities 140 as the staple drivers advance to eject staples, thereby pushing the adjunct 104 out of the connections cavities and off of the cartridge 132 during the deployment of the staples.

The adjunct 134, the cartridge 132, and use thereof is further described in U.S. Pat. No. 10,716,564 entitled "Stapling Adjunct Attachment" issued Jul. 21, 2020, which is hereby incorporated by reference in its entirety. Additional exemplary examples of releasably attaching adjuncts to staple cartridges, and uses thereof, are also described in U.S. Pat. No. 10,716,564.

Monitoring and/or tracking exposure of an adjunct and any drug(s) retained therein to one or more exposure conditions can provide any number of benefits. Exposure conditions, such as an environmental condition, can affect performance of the adjunct, e.g., longevity, and/or can affect performance of the drug(s) retained therein, e.g., viability, longevity, and potency. Viability of a drug generally refers to efficacy of the drug, e.g., the drug's ability to produce a particular effect. Longevity of an adjunct generally refers to a length of time the adjunct can produce a particular effect, such as the adjunct's ability to degrade or dissolve in a patient's body and thereby release drug(s) from the adjunct. Longevity of a drug generally refers to a length of time the drug can produce a particular effect. Potency of a drug generally refers to an amount of the drug needed to produce a particular effect. The monitoring or tracking of the adjunct and the drug(s) retained therein from the point of manufacture to administration, or a portion thereof, can allow for early identification of non-viable adjunct and non-viable drugs, as well as modification of a patient's treatment, e.g., providing additional drug dosage to a patient to compensate for a drug having experienced an exposure condition adversely affecting the drug's performance, and/or shelf-life based upon the exposure monitoring or tracking. Thus, monitoring and/or tracking exposure of an adjunct and any drug(s) retained therein may reduce the risk of implanting an adjunct that has been rendered ineffective due to exposure conditions, may reduce the risk of administering a drug at a dosage that has been rendered ineffective due to exposure conditions, and may reduce the risk of a non-viable drug being administered to a patient via implantation of the adjunct that retains the drug therein.

In general, systems and methods described herein include active or passive sensing mechanisms that can monitor at least one exposure condition of an adjunct and any drug(s) retained therein. In some instances, the active or passive sensing mechanisms can also track the extent of the adjunct's and drug(s)'s exposure (e.g., frequency, intensity, and/or duration). As a result, the information related to the exposure condition itself and/or the extent of exposure can be used to determine the effectiveness of the adjunct and any drug(s) retained therein prior to implantation of the adjunct and/or prior to distribution in commerce of the adjunct that retains the drug(s) therein.

The systems described herein can include a staple cartridge and an adjunct releasably coupled to the staple cartridge, such as any one or more of the staple cartridges and any one or more of the adjuncts discussed above. As also discussed above, the adjunct can retain one or more drugs therein, and the staple cartridge either can be fixedly coupled to a jaw of a surgical stapler or can be configured to be removably and replaceably coupled to a jaw of a surgical stapler.

Further, the systems described herein can also include at least one sensor that can be configured to monitor or detect at least one exposure condition of an adjunct and any drug(s) retained therein. Examples of exposure conditions include geographic location (e.g., as sensed by a location sensor configured to sense GPS or other location), time (e.g., as sensed by a timer or a clock device such as an atomic clock), date (e.g., as sensed by a timer), temperature (e.g., as sensed by a temperature sensor), ultraviolet (UV) exposure (e.g., as sensed by a UV sensor configured to sense UV level), pH (e.g., as sensed by a pH sensor configured to sense pH level), humidity (e.g., as sensed by a humidity sensor configured to sense humidity level), light (e.g., as sensed by a photo detector configured to sense light level), and oxygen exposure (e.g., as sensed by an oxygen ($O_2$) sensor configured to sense oxygen level). Alternatively, or in addition, the at least one sensor can be configured to track the frequency, duration, and/or intensity of an adverse exposure event experienced by the adjunct and any drug(s) retained therein prior to implantation of the adjunct, e.g., a temperature spike during transport or storage of the adjunct and any drug(s) retained therein as sensed by a temperature sensor configured to sense temperature and a timer configured to provide date and time stamp data for the sensed temperature data. U.S. Patent Pub. No. 2002/0014951 entitled "Remote Control For A Hospital Bed" published Feb. 7, 2002, and U.S. Patent Pub. No. 2007/0251835 entitled "Subnetwork Synchronization And Variable Transmit Synchronization Techniques For A Wireless Medical Device Network" published Nov. 1, 2007, further discuss various exemplary sensors and are incorporated by reference herein in their entireties.

Temperature can adversely affect performance of an adjunct. For example, a temperature above a predetermined maximum threshold temperature or below a predetermined minimum threshold temperature can cause the adjunct to begin to degrade before implantation of the adjunct in a body of a patient and that, therefore, the adjunct should no longer be used. Temperature can also adversely affect performance of a drug. For example, a temperature above a predetermined maximum threshold temperature or below a predetermined minimum threshold temperature can cause the drug to lose potency and that, therefore, the adjunct having the drug retained therein should no longer be used or, before the drug is retained in the adjunct, that the drug should be retained in the adjunct.

UV exposure can adversely affect performance of an adjunct. For example, a UV level above a predetermined maximum threshold UV level or below a predetermined minimum threshold UV level can cause the adjunct to begin to degrade before implantation of the adjunct in a body of a patient and that, therefore, the adjunct should no longer be used. UV level can also adversely affect performance of a drug. For example, a UV level above a predetermined maximum threshold UV level or below a predetermined minimum threshold UV level can cause the drug to lose potency and that, therefore, the adjunct having the drug retained therein should no longer be used or, before the drug is retained in the adjunct, that the drug should be retained in the adjunct.

Humidity can adversely affect performance of an adjunct. For example, a humidity above a predetermined maximum threshold humidity or below a predetermined minimum threshold humidity can cause the adjunct to begin to degrade before implantation of the adjunct in a body of a patient and that, therefore, the adjunct should no longer be used. Humidity can also adversely affect performance of a drug. For example, a humidity above a predetermined maximum threshold temperature or below a predetermined minimum threshold humidity can cause the drug to lose potency and that, therefore, the adjunct having the drug retained therein should no longer be used or, before the drug is retained in the adjunct, that the drug should be retained in the adjunct.

Geographic location can be indicative of temperature and/or humidity exposure since temperature and humidity can be known for a particular location at a particular date and time. Geographic location can also be indicative of whether the drug is approved for use in its current location, e.g., whether or not the drug is exposed to an inappropriate geographic location.

Light can adversely affect performance of a drug. For example, a light level above a predetermined maximum threshold light level can cause the drug to lose potency and that, therefore, the adjunct having the drug retained therein should no longer be used or, before the drug is retained in the adjunct, that the drug should be retained in the adjunct.

Oxygen can adversely affect performance of an adjunct. For example, exposure of the adjunct to an oxygen level above a predetermined maximum threshold oxygen level can cause the adjunct to lose sterility and/or begin to degrade before implantation of the adjunct in a body of a patient and that, therefore, the adjunct should no longer be used. If the adjunct is sealed in a sterile packaging unit, the oxygen exposure of the adjunct should not change until the packaging unit is opened for use. Thus, oxygen level being above a predetermined maximum threshold oxygen level at a particular date/time stamp can be indicative of sterility of the adjunct being lost and/or that the adjunct may have started to degrade such that the adjunct should no longer be used.

In some embodiments, a system can include two sensors. The first sensor can be associated with the adjunct (and thus also with any drugs retained therein) and/or a packaging unit for the adjunct (and thus also with any drugs retained therein), and the second sensor can be associated with the drug(s) itself. The packaging unit can contain one or more adjuncts. The one or more adjuncts in the packaging unit can be releasably coupled to a staple cartridge, which can be in the packaging unit as a standalone unit configured to be removably and replaceably seated in a jaw of an end effector of a surgical stapler or can be in the packaging unit already coupled to an end effector of a surgical stapler, such as by being fixedly seated in a jaw of the end effector or by being removably and replaceably seated in the jaw of the end effector.

As discussed in more detail below, the first and second sensors can be used to monitor exposure conditions of the adjunct and any drug(s) retained therein prior to the adjunct being implanted in a patient and thus before the drug(s) are administered to a patient. This may help ensure that at the time of implantation the adjunct can effectively release the drug(s) and that at the time of drug administration upon adjunct implantation and/or at time(s) thereafter, each of the one or more drugs is viable and is delivered at an effective dosage. Moreover, this monitoring may also aid in detection of non-viable adjuncts and/or non-viable drugs early on in the supply chain. As a result, manufacturers can recall non-viable adjuncts (and thus any drug(s) retained therein) at an early stage, e.g., prior to packaging and/or distribution, which may lead to decreased recall costs and avoid the potential health risks to the patients.

The first sensor can be configured to monitor at least one exposure condition of the adjunct and any drugs retained therein while the adjunct is seated in a staple cartridge (whether or not the staple cartridge is seated in a jaw of an end effector). Alternatively, or in addition, the first sensor can be configured to monitor at least one exposure condition of the adjunct and any drugs retained therein while the adjunct and any drugs retained therein are within the packaging unit. As such, the first sensor can be configured to monitor at least one exposure condition of the drug(s) after the drug(s) are associated with the adjunct, e.g., after the drug(s) have been retained by the adjunct but before the adjunct has been implanted in a patient. As a result, the first sensor can function as a shelf-life monitor for the drug(s) once the drug(s) are retained by the adjunct and as a shelf-life monitor for the adjunct having the drug(s) retained therein.

The second sensor can be configured to monitor at least one exposure condition of a drug from an initial time before the drug is associated with the adjunct to a second time in which the drug is associated with the adjunct and the first sensor is activated. For example, the second sensor can be configured to monitor at least one exposure condition of the drug through the entire drug supply chain process, or alternatively, during different stages thereof. In general, a drug's supply chain begins at manufacturing of the drug and proceeds in order to packaging of the drug, storage of the drug in its packaging, and distribution of the drug in its packaging. In one embodiment, the initial time is the time that the drug enters the supply chain, e.g., when the drug itself is manufactured.

The data acquired by the first sensor and/or second sensor can be communicated to a processor through a communications interface. The communications interface can be associated with the adjunct or a staple cartridge seating the adjunct therein, or alternatively within or on the packaging unit for the adjunct, as discussed above. The processor can be remote from or local to the adjunct. Further, the processor can be a component of a computer system, such as computer system 700, 800 shown in FIGS. 11 and 12, which are discussed further below. In use, once the data is received by the processor, the processor can process the data and provide a data output. In one example, the data output can be an expiration date of a drug retained by an adjunct, which can be determined by taking into account the data acquired by the first and/or second sensors. The processor can be configured to similarly process the data and provide a data output regarding the adjunct. For example, the processor can be configured to determine the expiration date by determining an elapsed amount of time after the drug has been associated with the adjunct, e.g., after the drug is retained by the adjunct, as indicated by the first sensor (or other sensor) or an elapsed amount of time after the drug itself is manufactured as indicated by the second sensor (or other sensor). The processor can also be configured to compare the determined elapsed amount of time with the drug's predetermined expiration date as set by the manufacturer (or other quality controller) to determine whether the expiration date has passed. The processor can also be configured to adjust the elapsed amount of time based on the data acquired by the first and/or second sensors to account for intensity and duration of any exposure condition of the drug since the drug's association with the adjunct (first sensor data) and/or since the drug's manufacture (second sensor data). The processor can be configured to access a lookup table that is stored in a memory and that stored predetermined metrics for the drug. The predetermined metrics can associate the drug with each of one or more exposure conditions and indicate the exposure condition's effect on the drug's expiration date, e.g., by indicating how much time the drug's expiration date should be adjusted downward (if at all) for particular time durations of the exposure condition.

In some embodiments, the drug's expiration date can be for a batch of the drug, for example, when the drug has yet to be retained by the adjunct. Alternatively or in addition, the drug's expiration date can be for the drug retained by the adjunct. Further, the processor can also be configured to provide a data output indicating that the batch of the drug and/or the drug in the adjunct is beyond its expiration date. For example, the data output can be in the form of a warning, such as a warning configured to be communicated via text and/or image display to a user such as by text message, email, display on a computer system's display screen, etc. The adjunct's expiration date can similarly be for a batch of the adjuncts, for example, when the adjunct has yet to be coupled to an end effector, e.g., before a staple cartridge releasably coupled to the adjunct has been coupled to an end effector. Alternatively or in addition, the adjunct's expiration date can be for the adjunct coupled to an end effector via a staple cartridge that is releasably coupled to the adjunct.

A warning as discussed herein can be to a user of the adjunct and/or to a third party (e.g., a manufacturer of the adjunct and/or the drug, a cloud service configured to communicate with hospitals and/or other medical facilities that provide adjuncts to users, etc.). Providing a warning to the user may help prevent the adjunct from being implanted, thereby helping prevent the drug from being delivered to a patient, and thus help avoid adverse patient effects and/or allow the user to obtain new adjunct for implantation. Providing a warning to the third party as a cloud service may (1) facilitate automatic product replacement by allowing the cloud service to automatically reorder the adjunct, staple cartridge coupled to the adjunct, and/or surgical stapler coupled to the staple cartridge that is coupled to the adjunct, (2) allow the cloud service to automatically generate a complaint report that is transmitted from the cloud service to another third party, e.g., a manufacturer of the adjunct and/or the drug, a medical professional intended to implant the adjunct, etc., that the other third party may use to evaluate their business, take remedial action, etc., (3) allow the cloud service to automatically generate a request to a quality control unit, such as a quality control team at the adjunct's and/or drug's manufacturer, for consultation of what step(s) the user, the user's health care provider (HCP), the adjunct's manufacturer, the drug's manufacturer, and/or another party should take, and/or (4) associate the particular adjunct (e.g., as identified with a product identification code included in the warning) with a serialization that can be traced to a specific distribution leg in the supply chain, should the excursion happen with the user then the adjunct and/or the drug may not be refundable or replaced due to a history of known user error and/or the user can be reminded of appropriate storage conditions for the adjunct (e.g., message shown on a display of a computer system, email sent to the user associated with the adjunct, a hospital or other medical care facility being informed of the user error(s) for discussion with the one or more parties responsible for proper storage and/or transport of the adjunct at the medical care facility, etc.).

Another example of the data output of the processor after the processor processes the data is an excursion condition state, which can be determined by taking into account the data acquired by the first and/or second sensors. For example, the processor can be configured to compare data received from the first sensor and/or second sensor with a predetermined threshold or range indicative of a safe environmental condition. If the received data is outside of the predetermined safe range, above the predetermined safe threshold, or below the predetermined safe threshold as appropriate for the particular environmental condition, the data output can be in the form of a warning indicating that the adjunct and any drugs retained therein, or the drug or adjunct before being associated with one another, has experienced at least one environmental condition during its life so far in the supply chain that its performance has been adversely affected enough such that the drug should not be retained in the adjunct or the adjunct retaining the drug therein should not be implanted.

The second sensor can also be configured to track different stages of the supply chain and the duration of each stage. Rushes or delays in the supply chain can also have an impact on adjuncts and drugs. For example, production or storage delays of the adjunct itself or the drug itself can negatively affect the shelf-life of the adjunct or the drug before the drug is retained by the adjunct. As such, in some embodiments, the second sensor can be configured to control the activation of the first sensor so as to prevent premature activation that can occur when the drug encounters unanticipated temporal events (rushes or delays) between the time of drug manufacture to the time the drug is retained by the adjunct. In this way, the activation of the first sensor can be tailored in response to temporal events in the supply chain. For example, the second sensor can transmit data to a processor through a communications interface, as discussed herein, and the processor can be configured to provide a data output to the first sensor that delays or expedites activation of the first sensor.

Various embodiments of sensors and sensor communication are further described in U.S. Patent Pub. No. 2007/0251835 entitled "Subnetwork Synchronization And Variable Transmit Synchronization Techniques For A Wireless Medical Device Network" published Nov. 1, 2007, which is incorporated by reference herein in its entirety.

Figure 13:
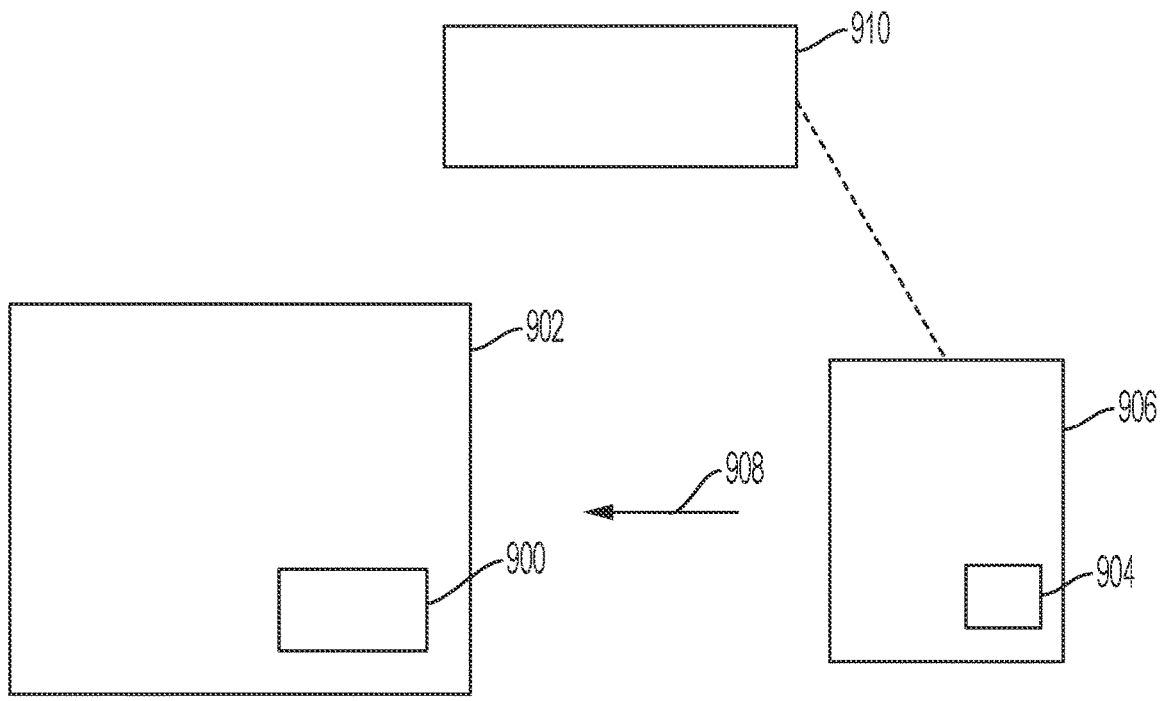
FIG. 13 is a schematic view of one embodiment of an adjunct associated with a first sensor and a drug associated with a second sensor.
Figure 14:
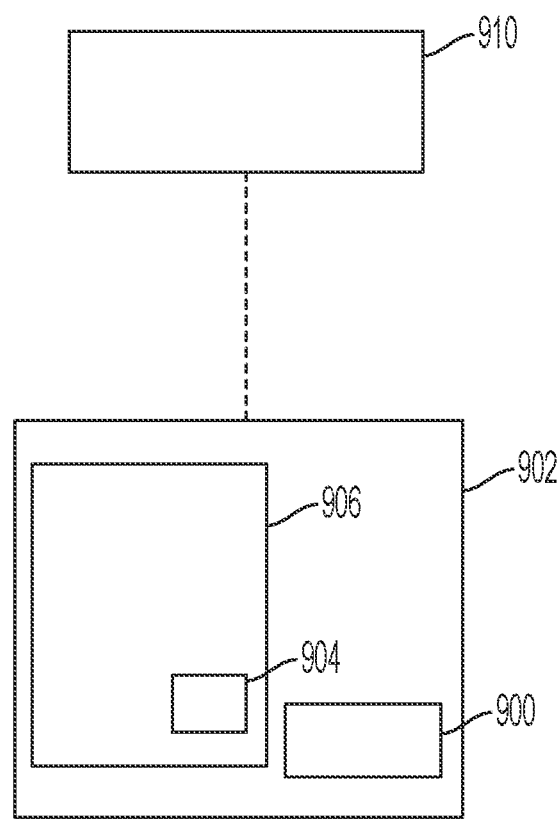
FIG. 14 is a schematic view of the adjunct, the drug, and the sensors of FIG. 13 with the adjunct retaining the drug therein.

FIG. 13 is a block schematic showing a first sensor 900 associated with an adjunct 902 and a second sensor 904 associated with a drug 906 that is configured to be retained by the adjunct 902. While not shown, the drug 906 can be disposed in a drug holder. The first sensor 900 can be associated with the adjunct 902 by, for example, being included on or in a staple cartridge that is releasably coupled to the adjunct 902 and/or by being on or in a packaging unit that is packaging the adjunct 902. The second sensor 904 can be associated with the drug 906 by, for example, being included on or in a drug holder holding the drug 906 therein and/or by being on or in a packaging unit that is packaging the drug 906 (and the drug holder holding the drug 906). As a result, the second sensor 904 can be configured to monitor at least one exposure condition of the drug 906 prior to the drug being associated with the adjunct 902 and the first sensor 900 being activated, as shown in FIG. 13. Further, in this illustrated embodiment, the second sensor 904 is in communication with a remote processor 910 such that the sensed data of the second sensor 904 can be transmitted thereto, as discussed above. Moreover, as shown, the drug 906 is still within a supply chain 908, which can begin at the time of manufacturing, until the drug 906 is retained by the adjunct 902 (FIG. 14).

Figure 15:
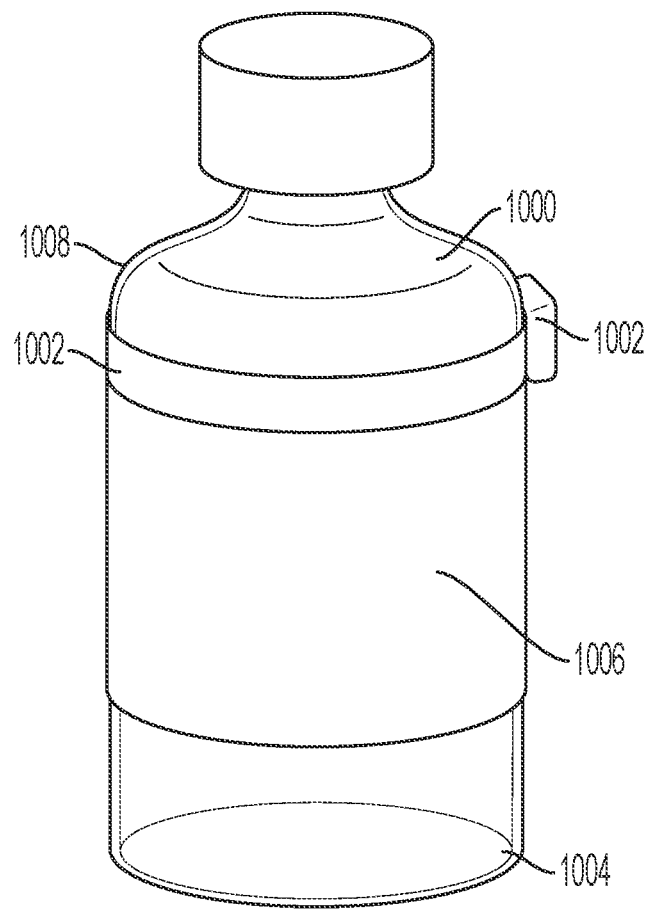
FIG. 15 is a perspective view of one embodiment of a drug holder having a sensor associated therewith.

FIG. 15 illustrates an exemplary drug holder 1000 having a sensor 1002, e.g., the first sensor 900, associated therewith.

The drug holder 1000 is shown in an example of packaging 1100. While the drug holder 1000 can have variety of configurations, in this illustrated embodiment, the drug holder 1000 includes a body 1004 defining a reservoir chamber configured to hold the drug 906 (obscured in FIG. 15). In other embodiments, the drug holder 1000 can have other configurations, shapes, and sizes. A label 1006 is disposed about a portion of an outer surface 1008 of the drug holder 1000. As shown, in this example the sensor 1002 is disposed on a portion of the label 1006. The sensor 1002 is configured to track at least one exposure condition of the drug 906 disposed within the drug holder 1000. For example, the sensor 1002 can be configured to track temperature and/or ultraviolet exposure throughout a time period, e.g., from the time the drug 906 is disposed within the drug holder 1000 to the time of administration, or any portion therebetween. Further, the sensor 1002 can be configured to log or store the tracking data. In certain embodiments, the sensor 1002 can also or instead be configured to track the expiration date of the drug 906.

Any data tracked by a sensor associated with a drug or adjunct can be communicated to a computer system. For example, as shown in FIG. 15, the packaging 1100 can include an electrical contact 1102 that is configured to read the sensed data from the sensor 1002. As shown in FIG. 15, the drug holder 1000 is disposed within the packaging 1100, and the sensor 1002 is positioned in close proximity to the electrical contact 1102. As such, once the sensor 1002 is positioned close to or in direct contact with the electrical contact 1102, the sensor 1002 is read by the electrical contact 1102 (e.g., a reader) and the data from the sensor 1002 is transmitted via communication interface(s) to a processor of a computer system, such as to the processor 896 via the communications interface 899 shown in FIG. 12. In this illustrated embodiment, the data is wirelessly transmitted to the processor. In other embodiments, the data is transmitted to the processor through a wired connection. As discussed in more detail below, the processor can compare the data against defined criteria and determine whether the data satisfies the criteria. In instances where the data does not satisfy the criteria, the processor can provide data output to allow for corrective action to be taken.

Referring again to FIG. 14, once the drug 906 is retained by the adjunct 902, as shown in FIG. 14, the drug is associated with the adjunct 902, and the first sensor 900 can be activated (e.g., by the second sensor 904). As a result, the first sensor 900 can be configured to monitor at least one exposure condition of the drug 906 after the drug 906 is retained by the adjunct 902. Further, in this illustrated embodiment, the first sensor 900 is in communication with the remote processor 910 such that the sensed data of the first sensor 900 can be transmitted thereto, as discussed above. As a result, the sensed data from the first and second sensors 900, 904 can be used to monitor the drug 906 from the time of manufacturing to the time of administration. In other embodiments, the first sensor 900 can be omitted while the second sensor 904 can be present such that the second sensor 904 is configured to monitor at least one exposure condition of the drug 906 and the adjunct 902 having the drug 906 retained therein.

In certain embodiments, the first and/or second sensors can have an independent exposure and shelf life. For example, the sensitivity of the first and/or second sensors can be affected over time by exposure to conditions, some of which can be representative of those experienced by the adjunct and the drug retained by (or to be retained by) the adjunct. This can allow for the compromised sensor to be replaced or for the adjunct and/or drug to not be used due to potentially inaccurate or unavailable sensor data. As such, in certain embodiments, a processor in operative communication with the first and/or second sensors can be configured to cause at least one warning to be provided indicating that the first sensor and/or second sensor has been compromised. In this way, a user can be afforded enough time to take any desired corrective action before the adjunct is implanted (although as mentioned above, the adjunct may ultimately not be implanted).

Figure 12:
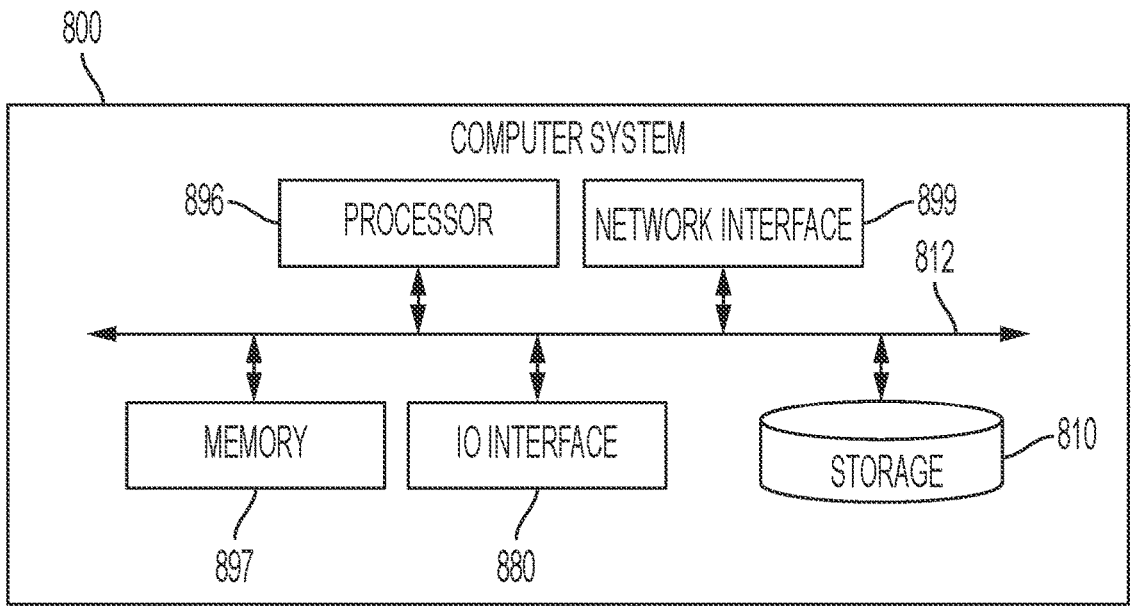
FIG. 12 is a schematic view of one embodiment of a computer system.

In certain embodiments, the processor is a component of a computer system, such as computer system 800 shown in FIG. 12, which can also include memory, e.g., the memory 897. As such, the first and second sensors and the processor can be part of a closed-loop feedback system. The stored data within the memory can include predetermined threshold(s) for one or more exposure conditions of the drug (relevant for first sensor data) and predetermined threshold(s) for one or more exposure conditions of the adjunct (relevant for second sensor data). During data sensing, the processor can receive feedback input from the sensor. The processor can aggregate the received feedback input(s), perform any necessary calculations, compare it to the predetermined threshold for the corresponding exposure condition and element (drug or adjunct), and provide data output.

Figure 16:
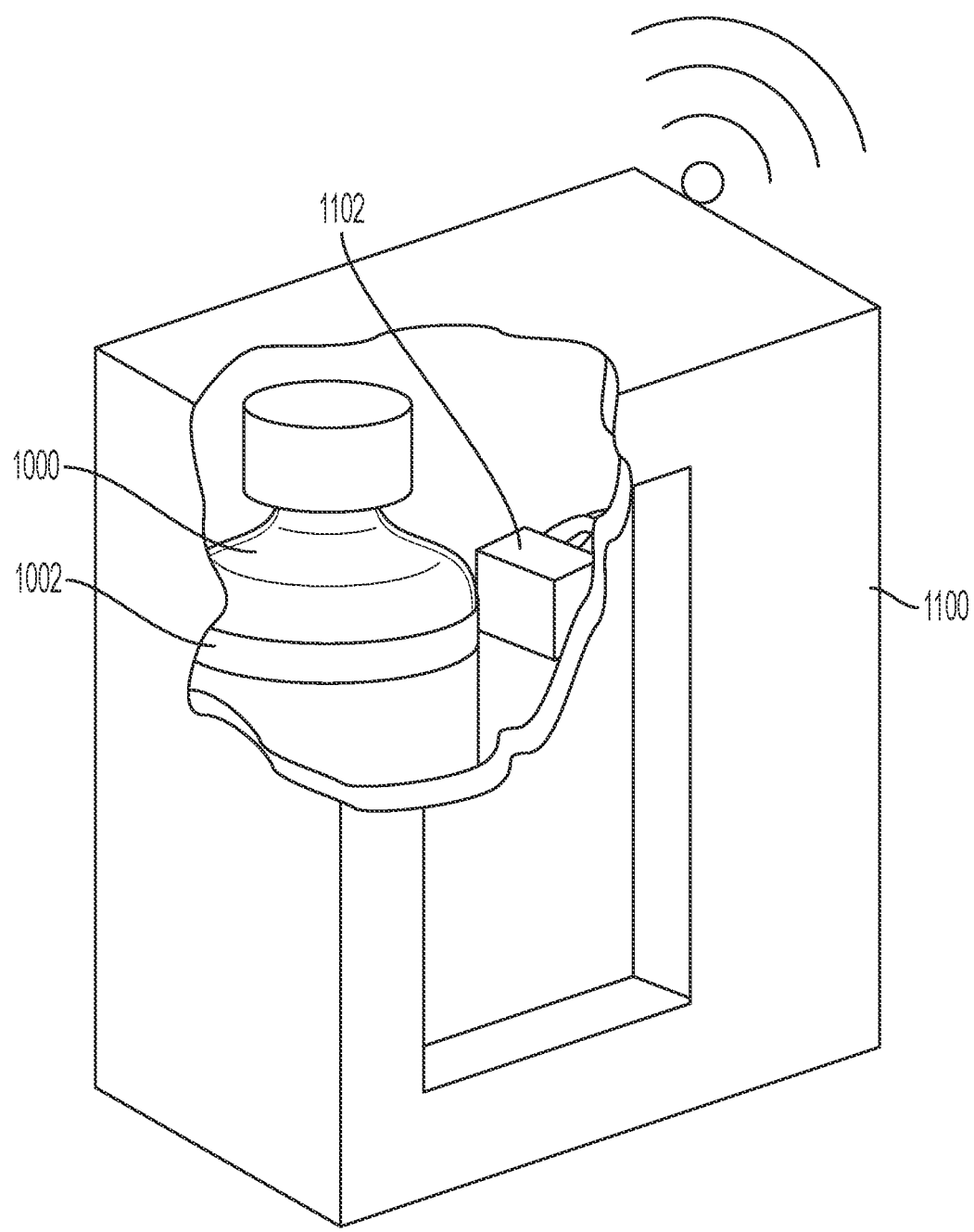
FIG. 16 is a perspective, partial cutaway view of the drug holder and sensor of FIG. 15 in packaging.
Figure 17:
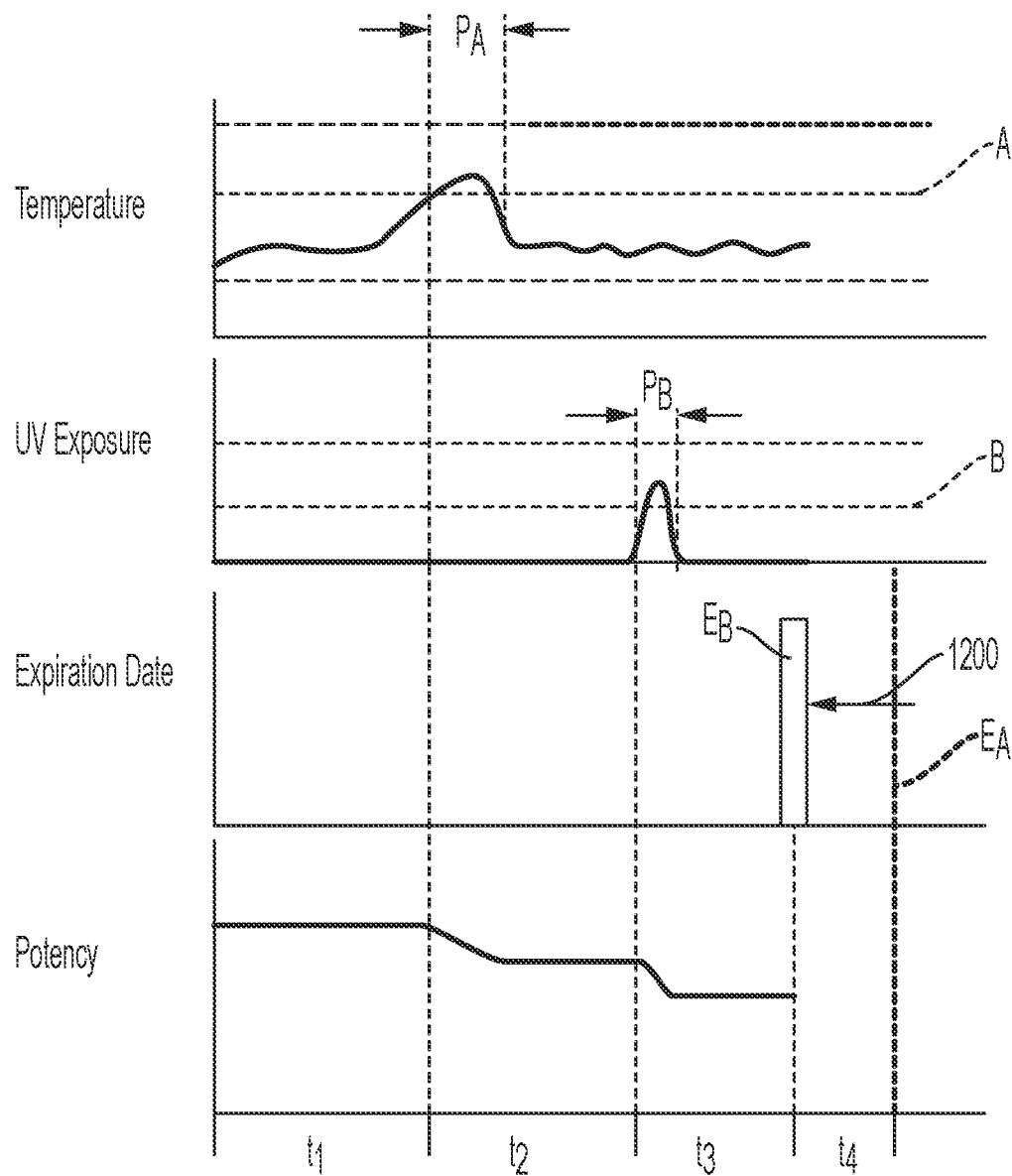
FIG. 17 is a graph illustrating one embodiment of sensor tracking of temperature, ultraviolet exposure, and expiration date throughout four time intervals.

For example, in one embodiment, as shown in FIG. 17, a sensor, such as the first sensor 900 of FIGS. 13 and 14, the second sensor 904 of FIGS. 13 and 14, and the sensor 1002 of FIGS. 15 and 16, can be configured to track temperature and ultraviolet exposure over four different time intervals $T_1$, $T_2$, $T_3$, $T_4$. A person skilled in the art will appreciate, however, that the following discussion is also applicable to other exposure conditions, e.g., humidity, pressure, etc.

In this exemplary embodiment, if the processor determines that the drug and/or the adjunct is being exposed to a temperature that exceeds a predetermined temperature control threshold (A) during any time interval, the processor is configured to transmit a data output characterizing the determination so that a warning can be provided as discussed above and/or to transmit a data output causing such a warning to be provided. In this illustrated embodiment, the processor determined that the exposure temperature of the drug exceeded the predetermined temperature control threshold A for a period of time, $P_A$, during the second time interval $T_2$. As shown, this increase in temperature for a period of time $P_A$ caused the potency of the drug to decrease. This is because the potency of the drug is a function of the intensity and duration of an exceeding exposure event. Further, the potency of the drug is also a function of the frequency of the exceeding exposure event.

Similarly, in this exemplary embodiment, if the processor determines that the drug and/or the adjunct is being exposed to UV that exceeds a predetermined UV control threshold B, the processor is configured to transmit a data output characterizing the determination so that a warning can be provided as discussed above and/or to transmit a data output causing such a warning to be provided. In this illustrated embodiment, the processor determined that the UV exposure of the drug exceeded the predetermined control threshold B for a period of time $P_B$, during the third time interval $T_3$. As shown, this increase in UV for a period of time $P_B$ caused the potency of the drug to further decrease.

Further, if a drug and/or an adjunct is exposed to an adverse exposure event, the drug's and/or the adjunct's shelf life can be affected. For example, as shown in FIG. 17, since the temperature and UV exposure exceeded the predetermined temperature control threshold and predetermined UV control threshold, respectively, the drug's shelf life was decreased, as denoted by arrow 1200. In particular, the shelf-life decreased from $E_A$ to $E_B$. This resulted in a loss of drug viability over the fourth time interval $T_4$. As such, the expiration date of the drug was expedited due to the exceeding temperature and UV exposure conditions experienced by the drug. Thus, the expiration date of the drug can be a function of the intensity and duration of any exposure condition of the drug. A person skilled in the art will therefore appreciate that in other instances, the drug's shelf-life can be increased, the adjunct's shelf-life can be increased, and/or the adjunct's shelf-life can be decreased.

In some embodiments, a system can include a status indicator and a reader that is configured to detect the status indicator. The status indicator can be configured to indicate an extent (e.g., frequency, intensity, and/or duration) of an exposure of the drug and/or the adjunct associated therewith to at least one environmental condition (e.g., temperature, UV exposure, humidity, etc.). For example, the status indicator can be responsive to an intensity and/or duration of an environmental condition.

The status indicator can have a variety of configurations. For example, in one embodiment, the status indicator can include a color change material that can be detected by the reader, e.g., an image sensor or other image capturing device configured to capture an image of the status indicator and provide the image to a processor for analysis, which can include comparison of the color of the status indicator in the image with previously captured image(s) of the status indicator to determine if a color change has occurred and/or a predetermined color designated as "normal" to determine if the current color of the status indicator deviates from normal. U.S. Patent Pub. No. 2012/0330684 entitled "Medication Verification And Dispensing" published Dec. 27, 2012, which is incorporated by reference herein in its entirety, further describes image capturing devices. The color change material can be used as a measure of exposure of the drug and/or the adjunct associated with the color change material to the at least environmental condition. That is, the color change material can be configured to change color when the drug and/or the adjunct associated therewith is exposed to an adverse environmental condition for a sufficiently long period of time. In use, this color change can be detected by the reader.

In other embodiments, the status indicator can include a reactive agent that can be configured to interact with a drug, e.g., the status indicator can be added to a segmented portion of a drug holder or a staple cartridge such as by being integrated into a material of the drug holder or staple cartridge. In use, if the drug is still viable, the interaction can create a specific color, fluorescence, and/or the like that can be detected by the reader, e.g., an image sensor or other image capturing device configured to capture an image of the status indicator and provide the image to a processor for analysis, which can include comparison of the color, fluorescence, etc. of the status indicator in the image with previously captured image(s) of the status indicator and/or a predetermined color, fluorescence, etc. designated as "normal." If the drug is non-viable, there is either no interaction or the resulting interaction creates a specific color, fluorescence, and/or the like that is undetectable by the reader.

In other embodiments, the status indicator can be a degradable element, e.g., a degradable circuit, that is impacted when exposed to an adverse environmental condition. That is, upon exposure to an environmental condition, the degradable element can degrade if the intensity and/or duration of the environmental condition exceeds a predetermined threshold. As such, the amount of degradation can be indicative of the condition of the drug and/or the adjunct associated with the degradable element, for example, at the time of implantation of the adjunct or at the time of the drug being retained by the adjunct. Further, this degradation can ultimately render the degradable element undetectable by the reader, e.g., an electrical circuit configured to communicate with the degradable circuit with ceasing of responses from the degradable circuit to requests from the reader being indicative of the degradable circuit having degraded or an image capturing device configured to capture an image of the status indicator with the degradable element no longer being visible in the image being indicative of the degradable element having degraded, thereby indicating that the drug and/or the adjunct associated with the degradable element is non-viable. Thus, the degradable element can function as a switch such that the detection or non-detection thereof signifies that the drug and/or the adjunct associated with the degradable element is viable or non-viable, respectively.

The degradable element can have a variety of configurations. In one embodiment, the degradable element can include one or more bioabsorbable and biocompatible polymers, including homopolymers and copolymers, that are configured to detect humidity levels experienced by the drug and/or the adjunct associated with the degradable element as the degradable element degrades in the presence of water. Examples of homopolymers and copolymers include p-dioxanone (PDO or PDS), polyglycolic acid (PGA), poly (lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. Other examples of copolymers include poly(lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima), poly(L-lactic acid) (PLLA), polyethylene terephthalate (PET), polyhydroxyalkanoate (PHA), a copolymer of glycolide and ε-caprolactone (PGCL), a copolymer of glycolide and -trimethylene carbonate, poly(glycerol sebacate) (PGS), polyesters, polyoxaesters, polyetheresters, polycarbonates, polyamide esters, polyanhydrides, polysaccharides, poly(ester-amides), tyrosine-based polyarylates, polyamines, tyrosine-based polyiminocarbonates, tyrosine-based polycarbonates, poly(D,L-lactide-urethane), poly (hydroxybutyrate), poly(B-hydroxybutyrate), poly(E-caprolactone), polyethyleneglycol (PEG), poly[bis (carboxylatophenoxy)phosphazene]poly(amino acids), pseudo-poly(amino acids), absorbable polyurethanes, poly (phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, polyamides, and combinations thereof. As understood by a person skilled in the art, degradation can be measured by ionizing the one or more polymers, or alternatively, doping the one or more polymers with a conductive material, which can allow for a resistive measure when the degradable element is in intact (undamaged). As such, the degradation of the one or more polymers is proportional to the degradation of the resistive circuit. Alternatively, or in addition, the degradable element can be formed of one or more copolymers, e.g., poloxamers, of different viscosity and/or molecular weight. In this way a predictable degradation profile can be created.

The reader can be in wired or wireless communication with a processor. As such, when the reader detects or is unable to detect the status indicator, this information can be transmitted to the processor. The processor can be configured to prompt a cue to a user when the reader stops or is unable to detect the status indicator as expected for a viable drug and/or adjunct, e.g., due to the degradation or color change of the status indicator in response being exposed to an environmental condition that exceeds a threshold exposure duration and/or a threshold exposure intensity.

In certain embodiments, the status indicator can be associated with an adjunct. For example, the status indicator can be on or within a staple cartridge having the adjunct releasably coupled thereto. Alternatively, the status indicator can be on a packaging for the adjunct, e.g., for a staple cartridge having the adjunct releasably coupled thereto. In one embodiment, the status indicator can be in the form of an electrochromic paste inserted on or within the staple cartridge, or alternatively on or within the packaging, that is configured to detect the exposure temperature during shipment and/or storage. In use, once the adjunct has reached a destination, the reader can be used to detect the status indicator and determine whether temperature limits were maintained during shipment.

Figure 18:
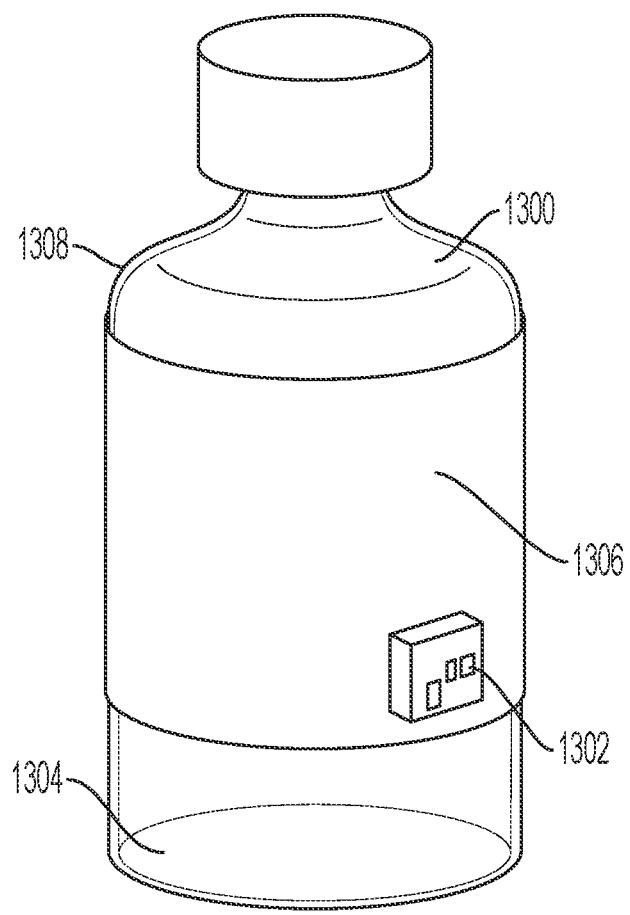
FIG. 18 is a perspective view of one embodiment of a drug holder having a status indicator associated therewith.

In other embodiments, the status indicator can be associated with a drug holder holding a drug that is configured to be retained by an adjunct. FIG. 18 illustrates an exemplary drug holder 1300 having a status indicator 1302 associated therewith. While the drug holder 1300 can have a variety of configurations, the drug holder 1300 in this example includes a body 1304 defining a reservoir chamber configured to hold a drug (not shown). In other embodiments, the drug holder 1300 can have other configurations, shapes, and sizes.

Figure 19:
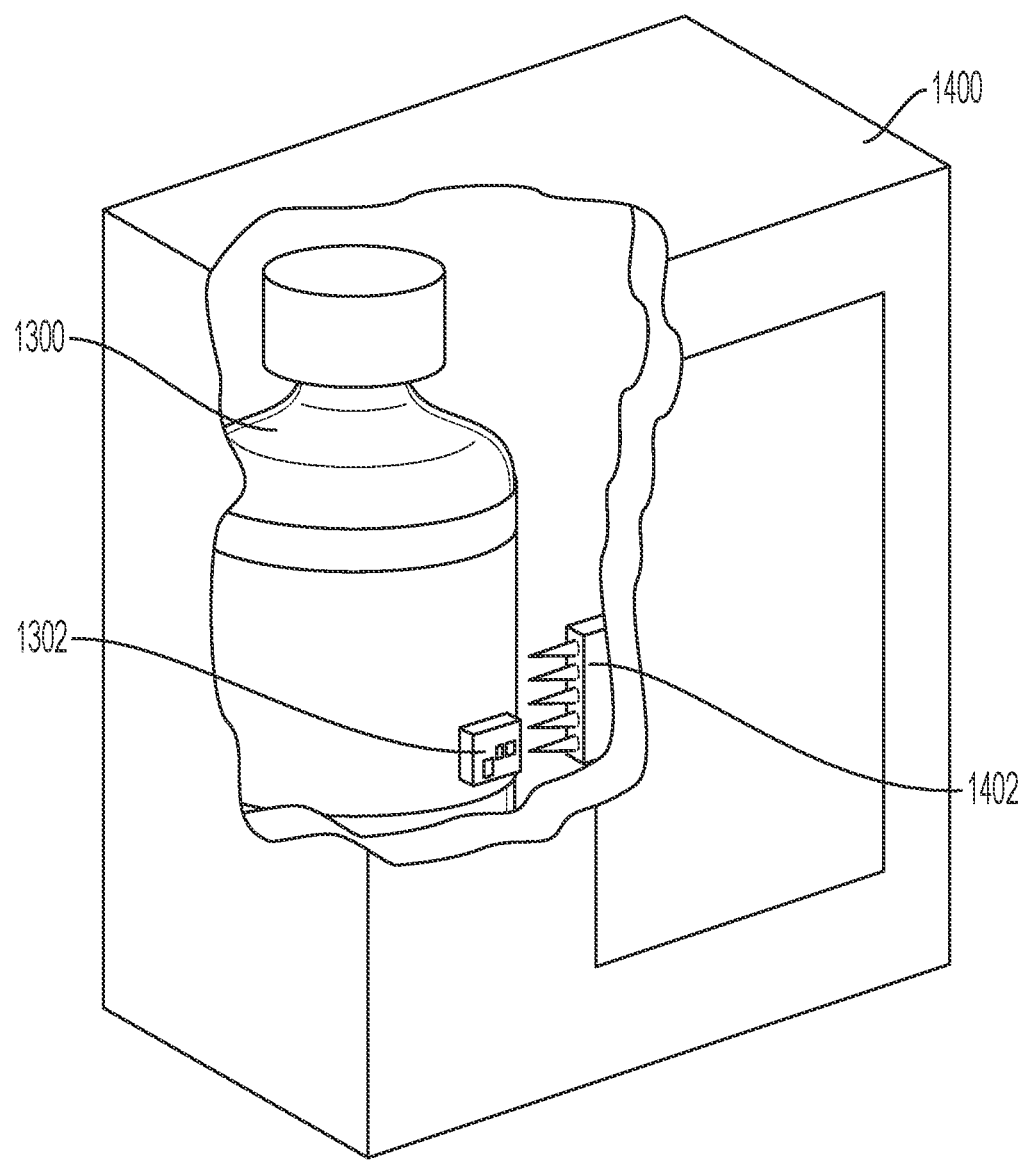
FIG. 19 is a perspective, partial cutaway view of the drug holder and sensor of FIG. 18 in packaging.

Further, as shown in FIG. 18, a label 1306 is disposed on an outer surface 1308 of the drug holder 1300. The label 1306 includes the status indicator 1302, which is configured to indicate an extent of exposure of the drug to at least one environmental condition. While the status indicator 1302 can have a variety of configurations, the status indicator 1302, as shown in FIG. 18, is a degradable circuit. As shown in FIG. 19, a reader 1402 within packaging 1400 in which the drug holder 1300 is disposed can be used to detect the degradable circuit 1302. The packaging 1400 can have any of a variety of configurations. In this illustrated embodiment, if the degradable circuit 1302 has been degraded, the reader 1402 will be unable to detect it, thereby indicating that the drug has been exposed to a temperature, a humidity, or an amount of ultraviolet light that has adversely impacted the drug to the point of non-viability.

In some embodiments, a system can include a label associated with an adjunct and/or a drug that is or is to be retained by the adjunct. The label can be configured to provide visual indication to a user that the drug and/or the adjunct has exceeded a predetermined exposure threshold for the drug and/or the adjunct. The predetermined exposure threshold can be associated with an exposure condition of the drug, e.g., temperature, UV exposure, etc.

For example, the predetermined exposure threshold can be a temperature threshold. The temperature threshold can include at least one of an absolute minimum temperature threshold, an absolute maximum temperature threshold, and a duration threshold below the absolute minimum temperature threshold or above the absolute maximum temperature threshold. In certain instances, a temperature threshold may be desired, particularly in instances where the drug and/or the adjunct is sensitive to temperature changes. Examples of temperature sensitive drugs include golimumab, ustekinumab, daratumumab, esketamine, ketamine, and guselkumab.

The label can include a variety of materials. In some embodiments, the label can include at least one electrochromic material and/or at least one thermochromic material. Examples of suitable thermochromic materials include at least one thermochromic ink. Thermochromic ink is configured to change color in response to temperature. Thermochromic ink has been used in consumer beverage packaging to show if the product is warm or cold and can be sunlight activated. Thermochromic ink has also been used in some forms to create glow-in-the-dark inks. Alternatively, or in addition, the label can include a reactive agent that is configured to interact with a drug within a drug holder and/or retained by an adjunct so as to trigger a visual change of at least a portion of the label when the drug has exceeded a predetermined exposure threshold.

In one embodiment, the label includes at least one electrochromic material. Examples of suitable electrochromic materials include at least one electrochromic ink. Electrochromic ink is configured to change color when an electric current is applied thereto. Electrochromic inks have been used in voltage checks on batteries and can be used within electrical circuits to indicate when a button, circuit, or portion the system is active. The electrochromic material can be configured to be a first color while in a first state, and then when transitioned to a second state, visually present a second color that is different than the first color. Alternatively, the electrochromic material can be configured to change its transparency state. In this way, the electrochromic material can be placed over printed information that would not be visible while the indicator is in a first state, but then when transitioned, information below could be viewed through the now transparent electrochromic material. Further, while the electrochromic material is described as having two states, a person skilled in the art will appreciate that some electrochromic materials can have more than two stable states. In use, the electrochromic material can be transitioned according to defined criteria stored within a processor for a particular drug and/or a particular adjunct associated with the label. As such, when the defined criteria has been satisfied, the processor transmits an electronic signal to the label to cause the electrochromic material to transition from the first state to the second state. For example, the defined criteria can be a temperature threshold for the drug and/or the adjunct.

The visual indication can be in a variety of forms, for example one or more words, numbers, letters, shapes, symbols, continuous or discontinuous designs or patterns, or any combination thereof. Alternatively, or in addition, the visual indication can be a color change of at least a portion of the label from a first color to a second color that is different than the first color.

Figure 20:
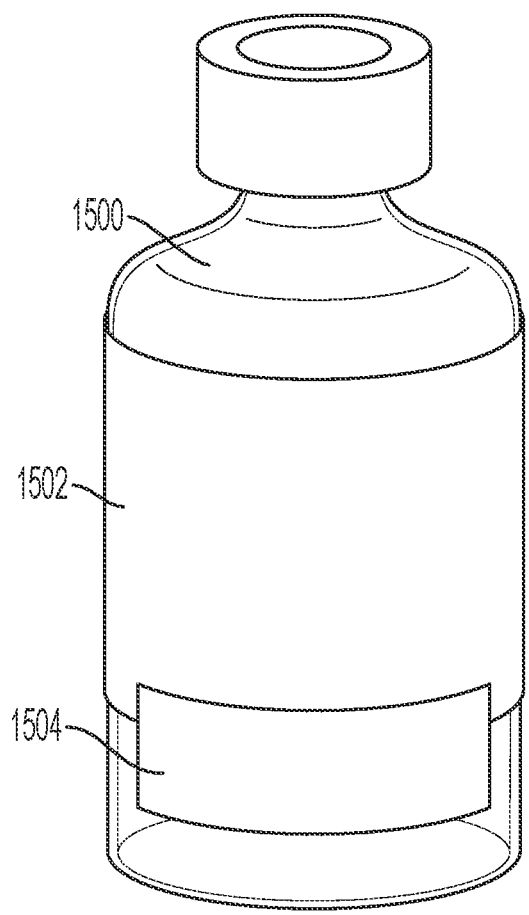
FIG. 20 is a perspective view of one embodiment of a drug holder having a label disposed thereon, the label being in a first state.
Figure 21:
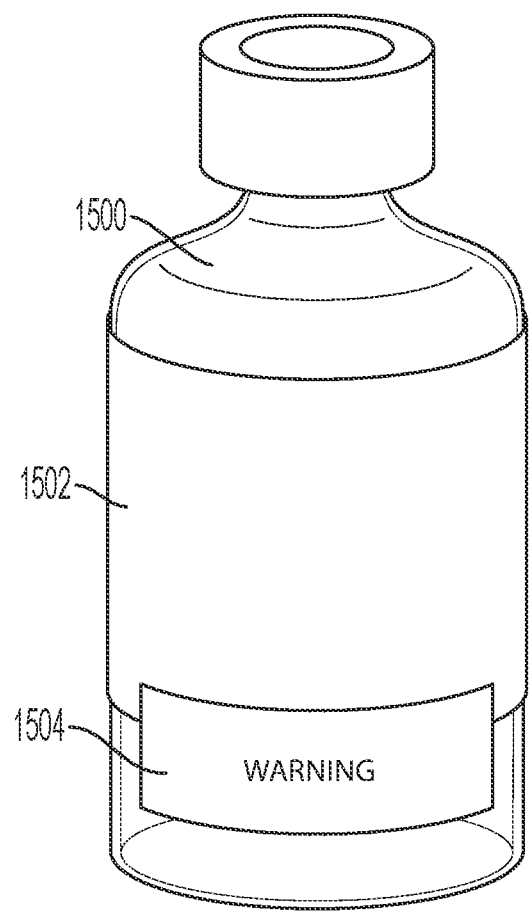
FIG. 21 is a perspective view of the drug holder and label of FIG. 21, the label being in a second state.

FIGS. 20 and 21 illustrate an exemplary drug holder 1500 having a label 1502 disposed thereon. While not shown, a drug is disposed within the drug holder 1500 and is configured to be retained by an adjunct. In this illustrated embodiment, the label 1502 includes an electrochromic ink 1504 printed thereon. The electrochromic ink 1504 is configured to provide a visual indication in response to the drug exceeding a temperature threshold. FIG. 20 shows the label 1502 in a first state in which the drug has not exceeded the temperature threshold. As shown, when the label 1502 is in the first state, the electrochromic ink 1504 is in a static initial state. That is, the electrochromic ink 1504 has not been triggered by a processor (not shown), which is in communication therewith, to transition to another state. In contrast, FIG. 21 shows the label 1502 in a second state in which the drug has exceeded the temperature threshold. As shown, when the label 1502 is in the second state, the electrochromic ink 1504 has transitioned from its initial state in such a way that formed the word "WARNING." A label similar to the label 1502 can be disposed on another element and be similarly used, such as on a packaging for the drug holder 1500 (or other drug holder) or on packaging for an adjunct that retains at least one drug therein.

Figure 11:
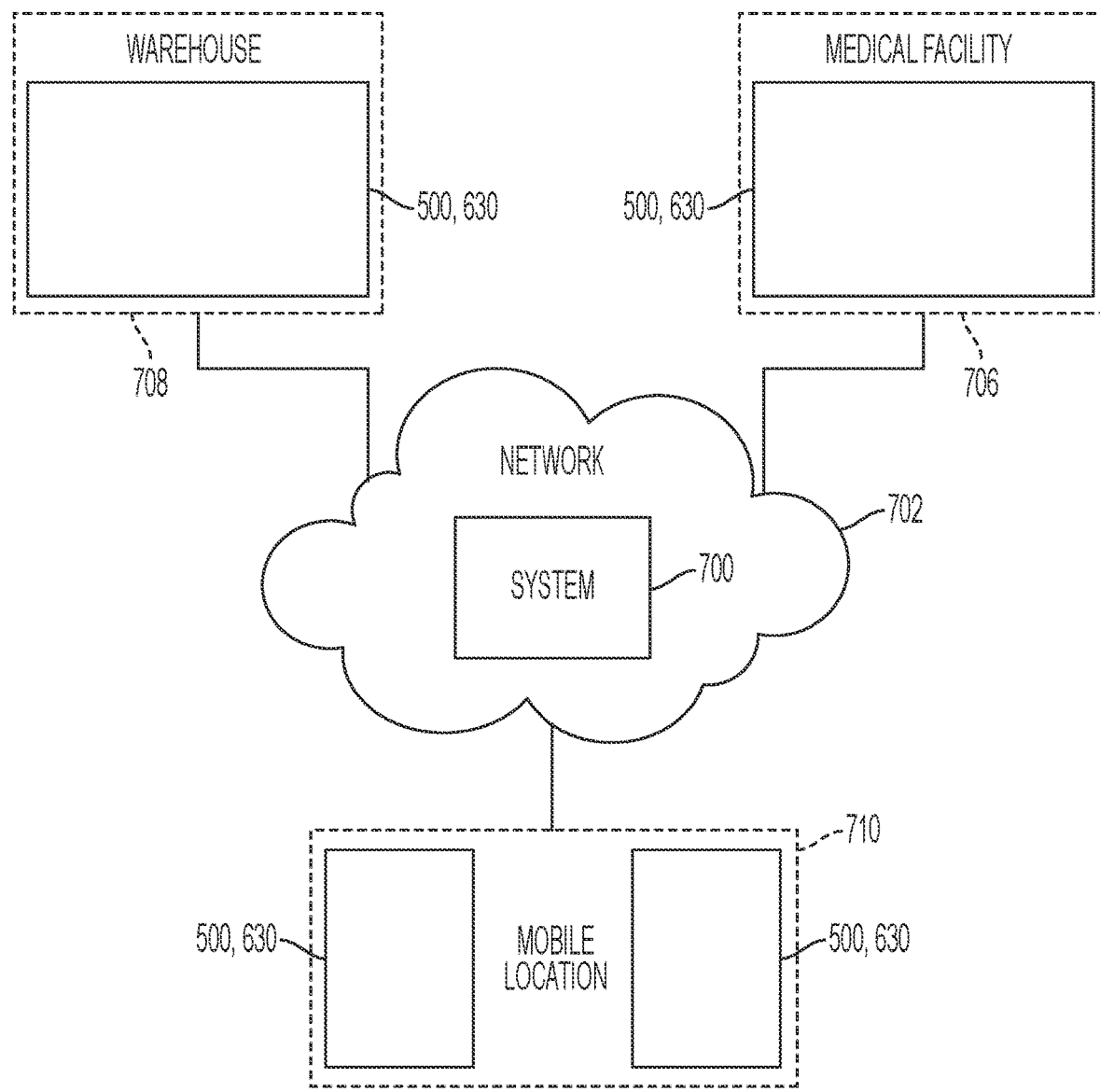
FIG. 11 is a schematic view of one embodiment of a communication network.

As mentioned above, a communications interface can be associated with an adjunct and/or a drug that is retained by or is configured to be retained by an adjunct, such as by being included within or on a drug holder holding the drug therein, within or on a staple cartridge or surgical stapler to which the adjunct is releasably coupled, or within or on packaging in which the adjunct and/or the drug is disposed. Such a communications interface can be configured to communicate with a computer system, such a central computer system 700 shown in FIG. 11. As shown in FIG. 11, a communications interface associated with an adjunct 500 and/or a drug 630 is configured to communicate with a central computer system 700 through a communications network 702 from any number of locations such as a medical facility 706 (e.g., a hospital or other medical care facility), a warehouse 708 (e.g., a distribution center or other stop in the adjunct's and/or drug's supply chain), or a mobile location 710 (e.g., between stops along the adjunct's and/or drug's supply chain). The communications interface can be configured to access the system 700 through a wired and/or wireless connection to the network 702. In an exemplary embodiment, the communications interface is configured to access the system 700 wirelessly, e.g., through Wi-Fi connection(s), which can facilitate accessibility of the system 700 from almost any location in the world.

A person skilled in the art will appreciate that the system 700 can include security features such that the aspects of the system 700 available to any particular user can be determined based on, e.g., the identity of the user and/or the location from which the user is accessing the system. To that end, each user can have a unique username, password, and/or other security credentials to facilitate access to the system 700. The received security parameter information can be checked against a database of authorized users to determine whether the user is authorized and to what extent the user is permitted to interact with the system, view information stored in the system, and so forth.

As discussed herein, one or more aspects or features of the subject matter described herein, for example components of the central computer system 700 and sensors, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As discussed herein, this feedback may be provided as a warning.

FIG. 12 illustrates one exemplary embodiment of the computer system 700, depicted as computer system 800. The computer system includes one or more processors 896 configured to control the operation of the computer system 800. The processor(s) 896 can include any type of microprocessor or central processing unit (CPU), including programmable general-purpose or special-purpose microprocessors and/or any one of a variety of proprietary or commercially available single or multi-processor systems. The computer system 800 also includes one or more memories 897 configured to provide temporary storage for code to be executed by the processor(s) 896 or for data acquired from one or more users, storage devices, and/or databases. The memory 897 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 also includes one or more network interface(s) 899 (also referred to herein as a communications interface), one or more input/output (IO) interface(s) 880, and one or more storage device(s) 810.

The communications interface(s) 899 are configured to enable the computer system to communicate with remote devices, e.g., other computer systems, over a network, and can be, for example, remote desktop connection interfaces, Ethernet adapters, and/or other local area network (LAN) adapters. The IO interface(s) 880 include one or more interface components to connect the computer system 800 with other electronic equipment. For example, the IO interface(s) 880 can include high speed data ports, such as universal serial bus (USB) ports, 1394 ports, Wi-Fi, Bluetooth, etc. Additionally, the computer system can be accessible to a human user, and thus the IO interface(s) 880 can include displays, speakers, keyboards, pointing devices, and/or various other video, audio, or alphanumeric interfaces. The storage device(s) 810 include any conventional medium for storing data in a non-volatile and/or non-transient manner. The storage device(s) 810 are thus configured to hold data and/or instructions in a persistent state in which the value(s) are retained despite interruption of power to the computer system. The storage device(s) 810 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 810 include a tangible or non-transitory computer readable medium configured to store data, e.g., a hard disk drive, a flash drive, a USB drive, an optical drive, a media card, a diskette, or a compact disc.

The elements illustrated in FIG. 12 can be some or all of the elements of a single physical machine. In addition, not all of the illustrated elements need to be located on or in the same physical machine.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

As shown in FIG. 11, the computer system 800 of FIG. 12 as described above may form the components of the central computer system 700 which is in communication with one or more communication interfaces each associated with at least one drug and/or at least one adjunct. Data, such as operational data of the adjuncts 500 and/or drugs 630, medical data acquired of patients associated with such adjuncts 500 and/or drugs 630 can be exchanged between the central computer system 700 and communication interface.

In an exemplary embodiment, the computer system 800 can be a single unit, e.g., a single server or as a single tower. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system can also include any of a variety of other software and/or hardware components, including by way of example, operating systems and database management systems. Although an exemplary computer system is depicted and described herein, it will be appreciated that this is for sake of generality and convenience. In other embodiments, the computer system may differ in architecture and operation from that shown and described here. For example, the memory 897 and storage device 810 can be integrated together or the communications interface 899 can be omitted if communication with another computer system is not necessary.

In an exemplary embodiment, the computer system to which data regarding an adjunct and/or a drug that is retained by or is configured to be retained by an adjunct, e.g., sensed data, data regarding a status indicator, etc., includes a surgical hub. Exemplary examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, and U.S. Pat. Pub. No. 2019/0201140 entitled "Surgical Hub Situational Awareness" filed Mar. 29, 2018, which are hereby incorporated by reference in their entireties.

In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as surgical devices that are used to conduct medical procedures on patients, sensors configured to monitor exposure conditions, etc. The surgical hubs provide a wide array of functionality to improve the outcomes of medical procedures. The data generated by the various surgical devices, sensors, and surgical hubs about the patient and the medical procedure may be transmitted to the cloud-based medical analytics system. This data may then be aggregated with similar data gathered from many other surgical hubs, sensors, and surgical devices located at other medical facilities. Various patterns and correlations may be found through the cloud-based analytics system analyzing the collected data. Improvements in the techniques used to generate the data may be generated as a result, and these improvements may then be disseminated to the various surgical hubs and surgical devices. Due to the interconnectedness of all of the aforementioned components, improvements in medical procedures and practices may be found that otherwise may not be found if the many components were not so interconnected. Various examples of structures and functions of these various components are described in more detail in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, and U.S. Pat. Pub. No. 2019/0201140 entitled "Surgical Hub Situational Awareness" filed Mar. 29, 2018.

Figure 22:
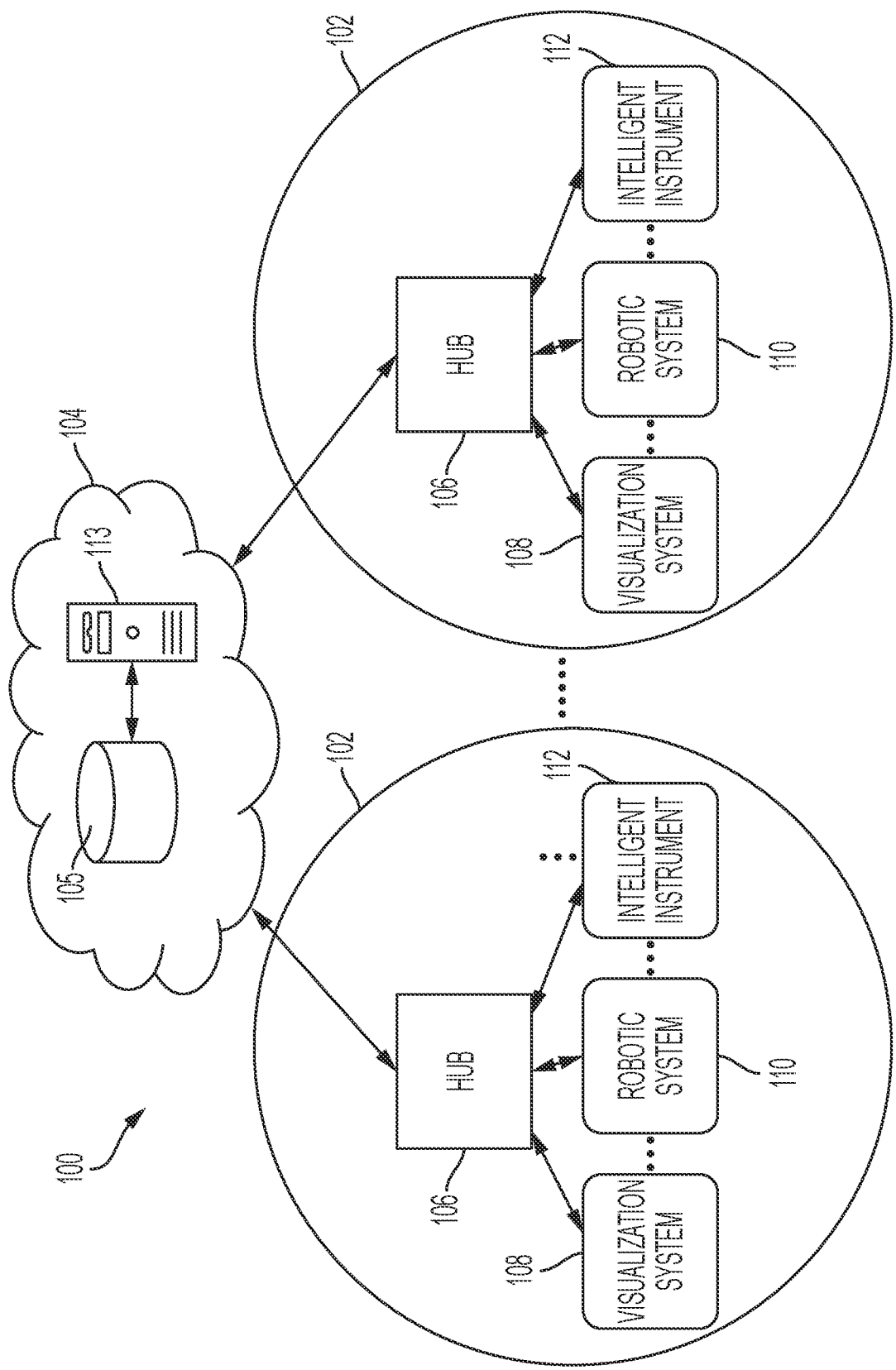
FIG. 22 is a schematic view of one embodiment of a computer-implemented interactive surgical system.

FIG. 22 illustrates an embodiment of a computer-implemented interactive surgical system 100 that includes one or more surgical systems 102 and a cloud-based system (e.g., a cloud 104 that can include a remote server 113 coupled to a storage device 105). Each surgical system 102 includes at least one surgical hub 106 in communication with the cloud 104. In one example, as illustrated in FIG. 22, the surgical system 102 includes a visualization system 108, a robotic system 110, and a handheld intelligent surgical instrument 112, which are configured to communicate with one another and/or the hub 106. The surgical system 102 can include an M number of hubs 106, an N number of visualization systems 108, an O number of robotic systems 110, and a P number of handheld intelligent surgical instruments 112, where M, N, O, and P are integers greater than or equal to one that may or may not be equal to any one or more of each other. Various exemplary examples of suitable robotic systems, visualization systems, cloud-based analytics, and surgical instruments that can be used in a computer-implemented interactive surgical system are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, and U.S. Pat. Pub. No. 2019/0201140 entitled "Surgical Hub Situational Awareness" filed Mar. 29, 2018.

The surgical instruments 112 in the system 100 can be various types of tools. In an exemplary embodiment, the surgical instruments 112 include surgical staplers configured to deliver an adjunct to tissue, such as the various surgical staplers and adjuncts discussed above. Thus, exposure conditions associated with adjuncts and drug(s) retained therein can be communicated from the surgical instruments 112 to their associated hubs 106 and from the hubs 106 to the cloud 104, such as by communication interfaces of the surgical instruments 112 each being configured to communicate sensed exposure condition data and other data to the their associated one of the hubs 106. The other data can include, for example, data relevant to use of the adjunct, such as a time the adjunct was implanted in a patient, e.g., a time the surgical instrument 112 was fired to deliver staples and the adjunct to tissue. The time the adjunct was implanted in the patient can facilitate storage and/or analysis of various useful metrics, such as surgical procedure outcomes, record of drug delivery to the patient, etc. Data analysis may further employ outcome analytics processing, and using standardized approaches may provide beneficial feedback to either confirm surgical treatments and adjunct and/or drug effectiveness or suggest modifications to surgical treatments, surgeon behavior, adjuncts, and/or drugs. For example, as discussed above, exposure conditions experienced by adjuncts and any drug(s) retained therein can be monitored and tracked, which may facilitate analysis of how exposure conditions experienced by the adjunct and/or the drug(s) retained by the adjunct affected surgical procedure outcomes, e.g., longer or shorter healing times, premature or delayed drug release from the adjunct, etc., that can be used to modify a patient's post-operative treatment and/or to modify future evaluation of exposure conditions to help post-operatively observed adverse effects due to exposure conditions be accounted for in the future by, e.g., changing thresholds for exposure conditions.

Figure 23:
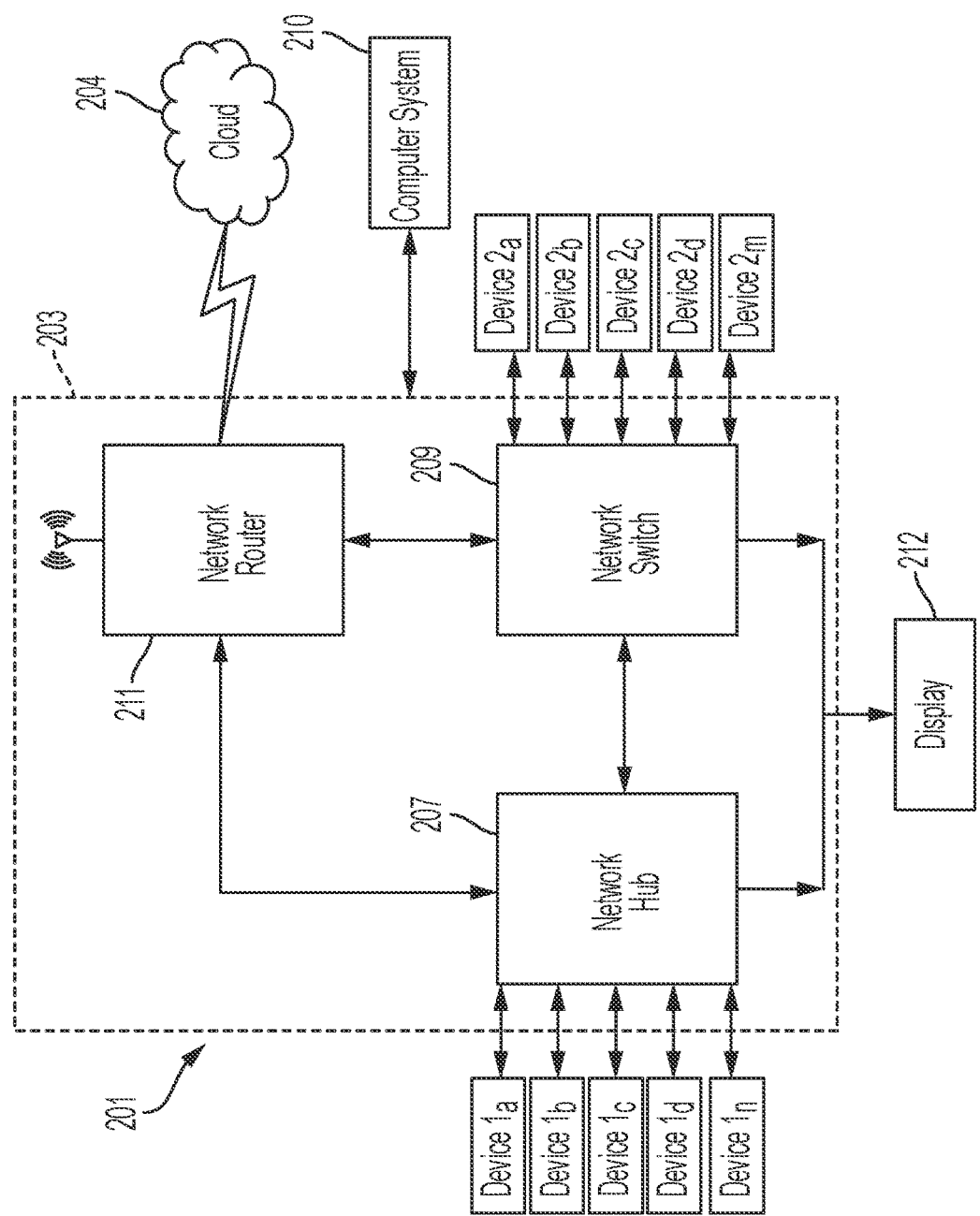
FIG. 23 is a schematic view of one embodiment of a surgical data network.

FIG. 23 illustrates one example of a surgical data network 201 comprising a modular communication hub 203, e.g., the hub 106, configured to connect modular devices located in one or more operating theaters of a healthcare facility, or any room in a healthcare facility specially equipped for surgical operations, to a cloud-based system including the cloud 204 that includes a remote server 213 coupled to a storage device 205, e.g., the cloud 104 that includes the remote server 113 coupled to the storage device 105. The modular communication hub 203 includes a network hub 207 and/or a network switch 209 in communication with a network router 211. The network hub 207, the network switch 209, and the network router 211 define the communication hub's communications interface. The modular communication hub 203 also can be coupled to a local computer system 210 to provide local computer processing and data manipulation. The surgical data network 201 can be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An "intelligent surgical data network" may be referred to as a "manageable hub" or "manageable switch." A switching hub reads the destination address of each packet and then forwards the packet to the correct port.

Modular devices $1_a$-$1_n$, e.g., any number of surgical instruments such as instruments 112, located in the operating theater can be coupled to the modular communication hub 203. The network hub 207 and/or the network switch 209 can be coupled to a network router 211 to connect the devices $1_a$-$1_n$ to the cloud 204 or the local computer system 210. Data associated with the devices $1_a$-$1_n$ can be transferred to cloud-based computers via the router for remote data processing and manipulation. Data associated with the devices $1_a$-$1_n$ can also be transferred to the local computer system 210 for local data processing and manipulation. Modular devices $2_a$-$2_m$ located in the same operating theater also can be coupled to a network switch 209. The network switch 209 can be coupled to the network hub 207 and/or the network router 211 to connect to the devices $2_a$-$2_m$ to the cloud 204. Data associated with the devices $2_a$-$2_n$ can be transferred to the cloud 204 via the network router 211 for data processing and manipulation. Data associated with the devices $2_a$-$2_m$ can also be transferred to the local computer system 210 for local data processing and manipulation. The numbers n, m of the devices $1_a$-$1_n$/$2_a$-$2_m$ can be the same as or different from one another.

A person skilled in the art will appreciate that the surgical data network 201 can be expanded by interconnecting multiple network hubs 207 and/or multiple network switches 209 with multiple network routers 211. The modular communication hub 203 can be contained in a modular control tower configured to receive multiple devices $1_a$-$1_n$/$2_a$-$2_m$. The local computer system 210 also can be contained in a modular control tower. The modular communication hub 203 is connected to a display 212 to display images obtained by at least some of the devices $1_a$-$1_n$/$2_a$-$2_m$, for example during surgical procedures.

The surgical data network 201 can include a combination of network hub(s), network switch(es), and network router (s) connecting the devices $1_a$-$1_n$/$2_a$-$2_m$ to the cloud 204. Any one of or all of the devices $1_a$-$1_n$/$2_a$-$2_m$ coupled to the network hub 207 or network switch 209 can collect data in real time and transfer the data to cloud computers for data processing and manipulation. Alternatively or in addition, any one or all of the devices $1_a$-$1_n$/$2_a$-$2_m$ coupled to the network hub 207 or network switch 209 can transfer previously collected data, such as exposure condition data, to cloud computers for data processing and manipulation, e.g., once the one or all of the devices $1_a$-$1_n$/$2_a$-$2_m$ is operatively connected to the cloud 204 via the communication hub 203. A person skilled in the art will appreciate that cloud computing relies on sharing computing resources rather than having local servers or personal devices to handle software applications. The term "cloud" can be used as a metaphor for "the Internet," although the term is not limited as such. Accordingly, the term "cloud computing" may be used herein to refer to "a type of Internet-based computing," where different services, such as servers, storage, and applications, are delivered to the modular communication hub 203 and/or the computer system 210 located in the surgical theater (e.g., a fixed, mobile, temporary, or field operating room or space) and to devices connected to the modular communication hub 203 and/or the computer system 210 through the Internet. The cloud infrastructure can be maintained by a cloud service provider. In this context, the cloud service provider can be the entity that coordinates the usage and control of the devices $1_a$-$1_n$/$2_a$-$2_m$ located in one or more operating theaters. The cloud computing services can perform a large number of calculations based on the data gathered by smart surgical instruments (and/or by components thereof, such as a staple cartridge releasably coupled to a smart surgical instrument), robots, and other computerized devices located in the operating theater. The hub hardware enables multiple devices or connections to be connected to a computer that communicates with the cloud computing resources and storage.

Applying cloud computer data processing techniques on the data collected by the devices $1_a$-$1_n$/$2_a$-$2_m$, the surgical data network may provide improved surgical outcomes, reduced costs, and/or improved patient satisfaction. At least some of the devices $1_a$-$1_n$/$2_a$-$2_m$ can be employed to view tissue states to assess leaks or perfusion of sealed tissue after a tissue sealing and cutting procedure. At least some of the devices $1_a$-$1_n$/$2_a$-$2_m$ can be employed to identify pathology, such as the effects of diseases, using the cloud-based computing to examine data including images of samples of body tissue for diagnostic purposes. This includes localization and margin confirmation of tissue and phenotypes. At least some of the devices $1_a$-$1_n$/$2_a$-$2_m$ can be employed to identify anatomical structures of the body using a variety of sensors integrated with imaging devices and techniques such as overlaying images captured by multiple imaging devices. The data gathered by the devices $1_a$-$1_n$/$2_a$-$2_m$, including image data, can be transferred to the cloud 204 or the local computer system 210 or both for data processing and manipulation including image processing and manipulation. The data can be analyzed to improve surgical procedure outcomes by determining if further treatment, such as the application of endoscopic intervention, emerging technologies, a targeted radiation, targeted intervention, precise robotics to tissue-specific sites and conditions, and drug administration may be pursued. Such data analysis can further employ outcome analytics processing, and using standardized approaches may provide beneficial feedback to either confirm surgical treatments and the behavior of the surgeon or suggest modifications to surgical treatments, surgeon behavior, adjuncts, and/or drugs.

The operating theater devices $1_a$-$1_n$ can be connected to the modular communication hub 203 over a wired channel or a wireless channel depending on the configuration of the devices $1_a$-$1_n$ to a network hub. The network hub 207 can be implemented as a local network broadcast device that works on the physical layer of the Open System Interconnection (OSI) model. The network hub provides connectivity to the devices $1_a$-$1_n$ located in the same operating theater network. The network hub 207 collects data in the form of packets and sends them to the router 211 in half duplex mode. The network hub 207 does not store any media access control/Internet Protocol (MAC/IP) to transfer the device data. Only one of the devices $1_a$-$1_n$ can send data at a time through the network hub 207. The network hub 207 has no routing tables or intelligence regarding where to send information and broadcasts all network data across each connection and to a remote server over the cloud 204. The network hub 207 can detect basic network errors such as collisions, but having all information broadcast to multiple ports can be a security risk and cause bottlenecks.

The operating theater devices $2_a$-$2_m$ can be connected to a network switch 209 over a wired channel or a wireless channel. The network switch 209 works in the data link layer of the OSI model. The network switch 209 is a multicast device for connecting the devices $2_a$-$2_m$ located in the same operating theater to the network. The network switch 209 sends data in the form of frames to the network router 211 and works in full duplex mode. Multiple devices $2_a$-$2_m$ can send data at the same time through the network switch 209. The network switch 209 stores and uses MAC addresses of the devices $2_a$-$2_m$ to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or the network switch 211 to cloud-based computer resources for further processing and manipulation of the data collected by any one of or all the devices $1_a$-$1_a$/$2_a$-$2_m$. The network router 211 can be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 can be implemented as a USB hub, which allows multiple USB devices to be connected to a host computer. The USB hub can expand a single USB port into several tiers so that there are more ports available to connect devices to the host system computer. The network hub 207 can include wired or wireless capabilities to receive information over a wired channel or a wireless channel. A wireless USB short-range, high-bandwidth wireless radio communication protocol cab be employed for communication between the devices $1_a$-$1_n$ and devices $2_a$-$2_m$ located in the operating theater.

In other examples, the operating theater devices $1_a$-$1_n$/$2_a$-$2_m$ can communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices $1_a$-$1_n$/$2_a$-$2_m$ can communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module can include a plurality of communication modules. For example, a first communication module may be dedicated to shorter-range wireless communications such as Wi-Fi and Bluetooth, and a second communication module can be dedicated to longer-range wireless communications such as GPS, EDGE, GPRS, CDMA, WiMAX, LTE, Ev-DO, and others.

The modular communication hub 203 can serve as a central connection for one or all of the operating theater devices $1_a$-$1_n$/$2_a$-$2_m$ and handle a data type known as frames. Frames carry the data generated by the devices $1_a$-$1_n$/$2_a$-$2_m$. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices $1_a$-$1_n$/$2_a$-$2_m$.

Figure 24:
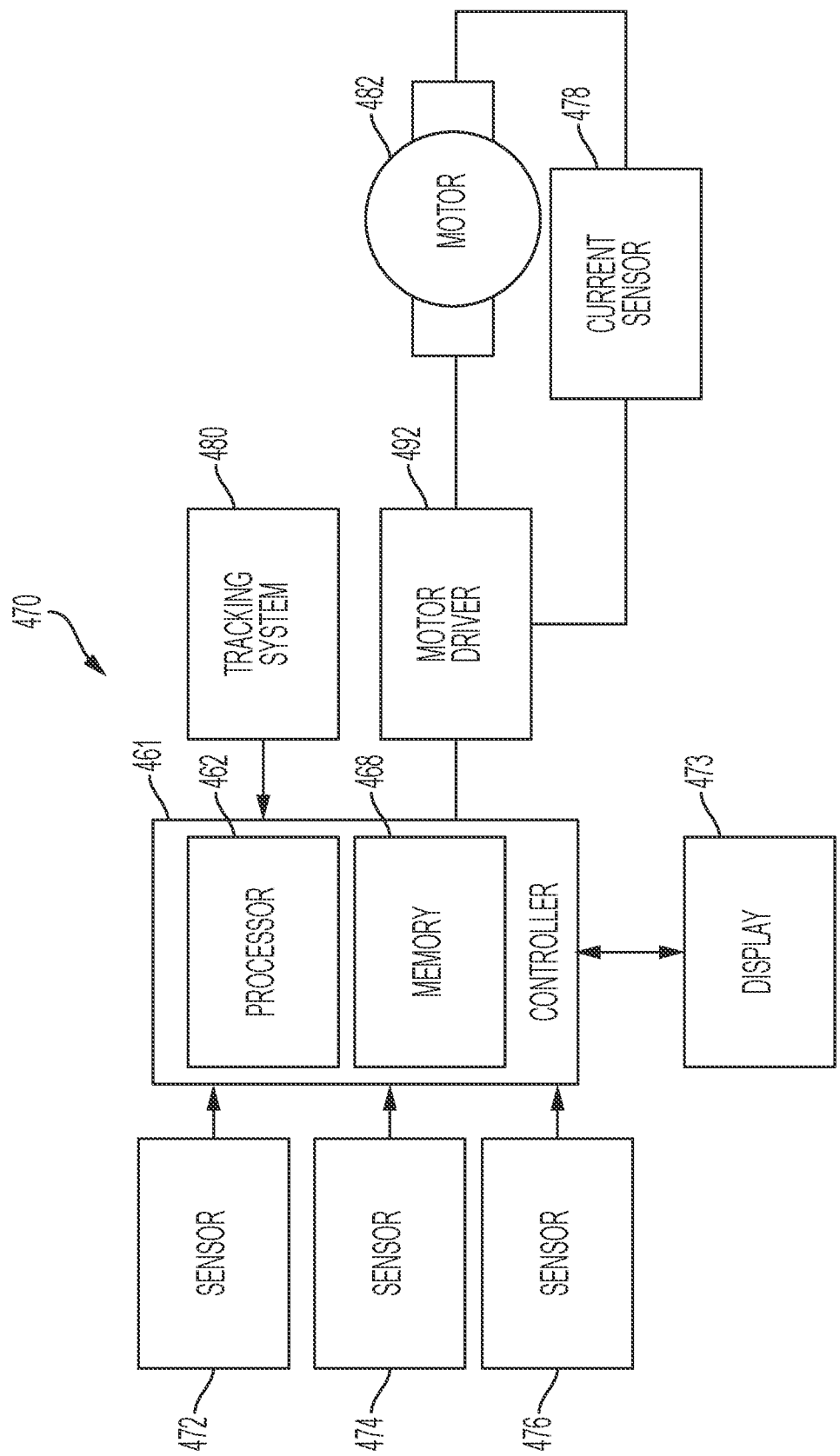
FIG. 24 is a logic diagram of a control system of a surgical instrument.

FIG. 24 illustrates an embodiment of a control system 470 of a surgical instrument or tool, e.g., a surgical stapler as described herein. The control system 470 includes a control circuit. The control circuit includes a microcontroller 461 including a processor 462 and a memory 468. A motor 482, driven by a motor driver 492, operably couples a longitudinally movable displacement member, such as a closure tube, a firing bar, an E-beam, and/or a knife, to fire staples, close jaws, and/or cut tissue, as discussed above. A tracking system 480 is configured to determine the position of the longitudinally movable displacement member. The position information is provided to the processor 462, which can be programmed or configured to determine the position of the longitudinally movable displacement member. Additional motors can be provided at the tool driver interface to control firing, closure tube travel, shaft rotation, and articulation. A display 473 displays a variety of operating conditions of the instrument and can include touch screen functionality for data input. Information displayed on the display 473 can be overlaid with images acquired via endoscopic imaging modules.

The microcontroller 461 can be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, including an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 461 can include a safety controller comprising two controller-based families such as TMS570 and RM4x, known under the trade name Hercules ARM Cortex R4, also by Texas Instruments. The safety controller can be configured specifically for IEC 61508 and ISO 26262 safety critical applications, among others, to provide advanced integrated safety features while delivering scalable performance, connectivity, and memory options.

The microcontroller 461 can be programmed to perform various functions such as precise control over the speed and position of knife and end effector articulation systems. The microcontroller 461 can be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The electric motor 482 can be a brushed direct current (DC) motor with a gearbox and mechanical links to an articulation or knife system. The motor driver 492 can be an A3941 available from Allegro Microsystems, Inc. Other motor drivers can be readily substituted for use in the tracking system 480 comprising an absolute positioning system. Further description of an absolute positioning system is provided in U.S. Pat. Pub. No. 2017/0296213 entitled "Systems And Methods For Controlling A Surgical Stapling And Cutting Instrument" published Oct. 19, 2017, which is hereby incorporated by reference in its entirety.

The motor 482 can be controlled by the motor driver 492 and can be employed by the firing system of the surgical instrument or tool. In various forms, the motor 482 can be a brushed DC driving motor having a maximum rotational speed of approximately 25,000 RPM. In other arrangements, the motor 482 can include a brushless motor, a cordless motor, a synchronous motor, a stepper motor, or any other suitable electric motor. The motor driver 492 can include an H-bridge driver comprising field-effect transistors (FETs), for example. The motor 482 can be powered by a power assembly releasably mounted to the handle assembly or tool housing for supplying control power to the surgical instrument or tool. The power assembly can include a battery, which can include a number of battery cells connected in series that can be used as the power source to power the surgical instrument or tool. In certain circumstances, the battery cells of the power assembly can be replaceable and/or rechargeable. In at least one example, the battery cells can be lithium-ion batteries which can be couplable to and separable from the power assembly. The motor driver 492 can be, for example, an A3941 available from Allegro Microsystems, Inc.

One or more of the control system's sensors 472, 474, 476, 478 can be configured to provide real-time feedback to the processor 462. At least one of the sensors 472, 474, 476, 478 can be configured to monitor at least one exposure condition as discussed herein. At least one of the sensor 472, 474, 476, 478 can be configured to monitor at least one operational parameter related to operation of the surgical instrument during a surgical procedure.

One example of a sensor configured to monitor an operational parameter includes a positon sensor configured to provide a unique position signal corresponding to the location of a displacement member, such as by being configured to measure linear displacement. Linear displacement sensors can include contact or non-contact displacement sensors. Examples of linear displacement sensors include linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, and any combination thereof.

Another example of a sensor configured to monitor an operational parameter is a strain gauge or a micro-strain gauge configured to measure one or more parameters of the surgical instrument's end effector. The measured strain is converted to a digital signal and provided to the processor 462. For example, the strain gauge or micro-strain gauge can be configured to measure an amplitude of strain exerted on the surgical instrument's anvil during a clamping operation, which can be indicative of closure forces applied to the anvil and indicative of tissue compression. For example, the strain gauge or micro-strain gauge can be configured to measure a force applied to tissue by the surgical instrument's end effector.

Another example of a sensor configured to monitor an operational parameter is a load sensor configured to measure the closure force applied by the surgical instrument's closure drive system to the anvil. The load sensor can be configured to measure a firing force applied to an E-beam (or an I-beam) in a firing stroke of the surgical instrument.

Another example of a sensor configured to monitor an operational parameter is a load sensor configured to measure a force used to operate the cutting element, e.g., knife, of the surgical instrument that cuts tissue captured between the end effector's jaws.

Another example of a sensor configured to monitor an operational parameter is a magnetic field sensor configured to measure thickness of tissue captured between the end effector's jaws. The measurement of the magnetic field sensor can be converted to a digital signal and provided to the processor 462.

Another example of a sensor configured to monitor an operational parameter is a current sensor 478 configured to measure current drawn by the motor 482. A force required to advance the firing member can correspond to the current drawn by the motor 482, for example. The measured force is converted to a digital signal and provided to the processor 462.

Measurements of exposure conditions, tissue compression, tissue thickness, and/or force required to close the end effector on tissue can be used by the microcontroller 461 to characterize the selected position of the firing member, the corresponding value of the speed of the firing member, and/or motor power level. For example, the memory 468 can store a technique, an equation, and/or a lookup table which can be employed by the microcontroller 461 in the assessment.

Sensors configured to sense operational parameters and uses of sensor-measured data, including to control operation of the surgical instrument using a robotic surgical system, are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, and U.S. Pat. Pub. No. 2019/0201140 entitled "Surgical Hub Situational Awareness" filed Mar. 29, 2018.

The control system 470 of the surgical instrument can include wired or wireless communication circuits to communicate with the modular communication hub as shown in FIG. 23.

In some instances, an adjunct and a drug may not have experienced any exposure conditions that adversely affect their performance but may still be unsuitable for use. In embodiments in which a staple cartridge is configured to be removably and replaceably coupled to an end effector of a surgical stapler, staples can only be fired out of the staple cartridge properly and/or safely if the staple cartridge is compatible with the surgical stapler. Staple cartridges have different sizes, so the staple cartridge removably and replaceably coupled to the end effector should have a size compatible with the particular end effector to which the staple cartridge is being coupled. Some surgical staplers may not be compatible with staple cartridges having an adjunct releasably coupled thereto, such as because the presence of the adjunct prevents the stapler's jaws from closing properly, because the presence of the adjunct prevents proper firing of staples because the stapler cannot provide sufficient force to drive the staples through the adjunct, and/or because the stapler's knife does not have sufficient sharpness and/or strength to cut an adjunct. It can therefore be important to establish compatibility between a surgical stapler and a staple cartridge having an adjunct releasably coupled thereto.

Establishing compatibility of a surgical stapler and a staple cartridge having an adjunct releasably coupled thereto generally involves determining whether the stapler and the staple cartridge (and adjunct releasably coupled thereto) are predetermined to be suitable for use with one another. The establishment of compatibility before staples are attempted to be fired from the stapler may help ensure that the stapler and the adjunct can each function properly and/or help ensure that the patient is not injured or otherwise harmed by use of a stapler that includes a staple cartridge and/or adjunct that is incompatible therewith and should not be used with the stapler.

In an exemplary embodiment, a method of establishing compatibility of a surgical stapler and a staple cartridge having an adjunct releasably coupled thereto includes acquiring first component data relating to the staple cartridge and/or the adjunct releasably coupled thereto, comparing the first component data with acceptable first component data, and setting an operational status of the surgical stapler based on the comparison of first component data with acceptable first component data.

The method of establishing compatibility of a surgical stapler and a staple cartridge having an adjunct releasably coupled thereto may ensure that the correct staple cartridge and adjunct is utilized with the stapler. This may reduce a risk of inadvertently using unsuitable components that may lead to malfunction of the stapler, cartridge and/or adjunct, to improper or entirely absent staple deployment, and/or to incorrect implantation of the adjunct, each of which may be dangerous for the patient.

The method can establish the compatibility of the stapler with only one of the cartridge and the adjunct releasably coupled to the adjunct or can establish the compatibility of the stapler with each of the cartridge and the adjunct releasably coupled to the adjunct. The stapler being compatible with only one of the cartridge and the adjunct releasably coupled to the adjunct can be indicative of the other of the cartridge and the adjunct releasably coupled to the adjunct being compatible with the stapler, e.g., because only certain size adjuncts can be used with certain size cartridges, because only certain adjuncts can be used with certain cartridges, etc.

Acquiring the first component data can include communicating the first component data from the component to an external device. Alternatively, acquiring the first component data can include communicating the first component data from the component to another component, such as a processor, e.g., a processor of a surgical hub. The processor can be the same processor used for comparing the first component data with the acceptable first component data and for setting the operational status of the stapler, or the processor can be a different processor.

Communicating the first component data can include communicating the first component data from a data storage component. The first component can include the data storage component. Examples of data storage components are an integrated circuit, a radio frequency identification (RFID) tag, and a bar code. The first component data can be stored utilizing a single data storage component or a plurality of data storage components. If a plurality of data storage components are used, each can be different from one another, which may help provide redundancy and/or allow for first component data retrieval even if a certain type of data communication is currently unavailable, e.g., if an RFID scanner is absent or damaged. Acquiring data (e.g., the first component data) from the data storage component requires the use of an appropriate communications interface for receiving the data, such as an RFID scanner, a bar code scanner, or integrated circuitry.

Comparing the first component data with the acceptable first component data can utilize a processor. The processor can be part of the stapler or can be part of an external device that is external to the stapler. The acceptable first component data can be stored in a memory. The memory can be part of the stapler or can be part of the external device. When the processor is part of the stapler it is preferable that the memory is part of the stapler as well to avoid the need to communicate with an off-board memory. Similarly, when the processor is part of the external device, it is preferable that the memory is part of the external device as well to avoid the need to communicate with an off-board memory.

Comparing the first component data with the acceptable first component data can include comparing first component parameter(s) of the first component data with acceptable parameter(s) of the acceptable first component data. The comparison includes determining whether each of one or more first component parameters in the first component data matches a corresponding parameter in the acceptable first component data, with a match indicating compatibility and a mismatch indicating incompatibility.

The acceptable first component data can be updatable. Therefore, the suitability of the stapler with various cartridges and adjuncts can be updated based on developments in relation to the cartridge and adjunct and the stapler. The stapler can include a communications interface configured to receive the updated acceptable first component data and store the updated acceptable first component data in the memory.

Setting the operational status of the stapler can be based on the comparison of the first component data with acceptable first component data. Setting the operational status can include maintaining the operational status of the stapler, e.g., allowing for operation of the stapler, if the first component data is determined to correspond with the acceptable first component data. When the first component data is determined not to correspond to the acceptable first component data, the operational status of the stapler can be changed from the stapler being operational for tissue clamping and staple and adjunct delivery to not being operational for tissue clamping and staple and adjunct delivery (or can remain as being not operational for tissue clamping and staple and adjunct delivery if already set to not being operational for tissue clamping and staple and adjunct delivery). Alternatively, the operational status of the stapler can be changed from the stapler not being operational for tissue clamping and staple and adjunct delivery to being operational for tissue clamping and staple and adjunct delivery (or can remain as being operational for tissue clamping and staple and adjunct delivery if already set to operational for tissue clamping and staple and adjunct delivery) when the first component data corresponds to the acceptable first component data. The adopted approach can be dictated based on whether a default operational status of the stapler is to be the operational status or to be an inhibited operational status in which tissue clamping and staple and adjunct delivery is not possible but other operation(s) may be possible, such as comparing first component data with acceptable first component data, providing user notification(s) on a user interface of the stapler and/or via a surgical hub, etc. For example, if the default operational status is the inhibited operational status, e.g., where tissue clamping and staple and adjunct delivery is prevented but other operation(s) are possible, the operational status can be changed to be the operational status when the first component data is determined to corresponds to the acceptable first component data and any other component data (e.g., second component data for a second component, third component data for a third component, etc.) that may be assessed corresponds to its acceptable component data.

Acquiring the first component data can be carried out on the external device. The external device utilized as part of the first component data comparison can be the same external device that is used as part of establishing the dosing parameters.

The external device may be a smart device. The external device can be a device dedicated to the function of establishing the compatibility of the components of the drug administration device. Alternatively, the external device can be a device that performs other functions, such as a surgical hub, a smart phone, a tablet, a smart watch, etc. This multi-functional capability enables a user of the drug administration device to utilize an existing device for establishing the compatibility of components with the stapler, which may make checking for compatibility more likely to occur properly and without delay since users are already in the habit of keeping such an external device on their person or otherwise nearby for fast accessibility.

Comparing the first component data with the acceptable first component data can occur on the external device, which may be particularly efficient when the external device acquires the first component data.

Comparing the first component data with the acceptable first component data can utilize a processor of the stapler, e.g., processor that is part of the first component. Using a processor of the stapler may be particularly efficient when the first component receives the acceptable first component data from another source, such as another component of the stapler. In embodiments in which the first component receives the acceptable first component data, the first component can be configured to carry out the comparison on the processor and communicate the determined compatibility to the rest of the stapler as needed, e.g., by communicating the compatibility determination to a processor of the stapler, thus allowing for control of the operability of the stapler based on the compatibility of the first component.

The first component data can include image data. This image data can be acquired by imaging the cartridge, the adjunct, and/or the stapler with the external device. The external device can include an image sensor or other image capturing device. The use of image data as the first component data allows the user to take an image of the cartridge, the adjunct, and/or the stapler in order to facilitate assessment of the compatibility of the components. Taking an image is an action that many users will be familiar with, and so this approach will not be considered onerous by most users.

When the first component data includes image data, the comparison of the first component data with the acceptable first component data can include assessing the image data for particular markers or patterns representative of one or more particular components. For example, the assessment of the image data can include the processor extracting particular markers or patterns on an external surface of each of the component(s) to assess whether it is a compatible component. In this case, the user can be instructed to image the cartridge, the adjunct, and/or the stapler in such a manner that allows the acquisition of this marker or pattern data. In order to assist with this, the marker or pattern data can be present at a plurality of locations of the cartridge, the adjunct, and/or the stapler of interest.

Acquiring the first component data can include communicating the first component data from the first component to the processor of the stapler.

Setting the operational status of the stapler can include flagging that the operational status should be fully operational when the first component data corresponds with the acceptable first component data, and flagging that the operational status should not be fully operational when the first component data does not correspond with the acceptable first component data. Flagging the operational status can include writing data to a memory e.g., the memory of the stapler or the external device, that indicates that the operational status should be fully operational (or not be fully operational) based on the comparison of the first component data with the acceptable first component data. This flag data can then be read as needed in assessing the compatibility of components.

The flagging in relation to the first component data can be incorporated into a wider approach that involves a plurality of flags that are each set to indicate whether the operational status should be fully operational based on whether certain criteria are fulfilled. For example, one or more additional flags can be associated with the compatibility of components beyond the first component. In this way, setting the operational status of the stapler can include setting the operational status as fully operational when all of the flags (the flag for the first component and the one or more additional flags) indicate that the operational status should be fully operational and setting the operational status as not fully operational when any of the flags (the flag for the first component and the one or more additional flags) indicates that the operational status should not be fully operational. This multi-flag approach allows the operational status to be set based on a range of different criteria and thus effectively operates as a check list when required for an assessment of whether the stapler should be operational or not for tissue clamping and staple and adjunct delivery. For example, setting the operational status of the stapler can include flagging that the operational status should be fully operational for tissue clamping and staple and adjunct delivery only when the first component data corresponds with the acceptable first component data, and when second component data corresponds with acceptable second component data, and so on in relation to one or more additional components of interest. One example of a second component is a generator configured to provide energy to the stapler for energy delivery to clamped tissue.

Although it is described that the flags can be used to assess whether the stapler should be fully operational for tissue clamping and staple and adjunct delivery, the presence of the flags can be used in setting various variable parameters of the stapler as appropriate, e.g., in determining whether energy delivery from the stapler to tissue is possible, allowing end effector opening but not closing, etc. Therefore, the operational status can be set appropriately in view of the flags that are present. As noted above, these flags can be in the form of data (so-called "flag data") that is written to memory. This flag data can then be read for use in assessing whether the stapler should be fully operational.

The first component data can include an indication of at least one of a type of each of one or more drugs retained by the adjunct coupled to the staple cartridge, a provenance of the drug, a concentration of the drug(s) retained by the adjunct, an expiry date of the drug(s) retained by the adjunct, and a volume of drug(s) retained by the adjunct. This first component data related to the drug can be useful in analyzing surgical outcomes, etc. as discussed above since it can confirm which one or more drugs are delivered to a patient.

When the first component data relates to feature(s) of the first component itself, then the comparison of the first component data with the acceptable first component data can be made with known acceptable forms of the first component. For example, the first component data can convey a type of the staple cartridge, and the comparison of the first component data and the acceptable first component data can include comparing the type of staple cartridge with known acceptable staple cartridge type(s) for the stapler (e.g., as indicated in a lookup table stored in a memory accessible to the processor executing the comparison), and thus allow for setting the operational status of the stapler accordingly. For another example, in addition to or instead of the first component data conveying a type of the staple cartridge, the first component data can convey a type of the adjunct and the comparison of the first component data and the acceptable first component data can include comparing the type of the first component data can convey a type of the with known acceptable the first component data can convey a type of the type(s) for the stapler (e.g., as indicated in a lookup table stored in a memory accessible to the processor executing the comparison), and thus allow for setting the operational status of the stapler accordingly.

The first component data can include an indication of compatible firing parameters. In this way, the first component data can indicate what one or more firing settings, e.g., motor speed, cutting element speed, tissue clamping force, etc., are suitable for operating with the first component.

The first component data can include an indication of compatible cartridge and/or adjunct parameters. In this way, the first component data can directly indicate type(s) of cartridges and/or adjuncts that can be used with the stapler.

The first component data can be encoded on the first component. In other words, the first component data can be present on the first component. This encoding on the first component may ensure that the first component has the first component data readily accessible and may reduce a risk that the first component data becomes separated from the first component and thus be unavailable for access for assessing compatibility of the first component with the stapler.

Figure 25:
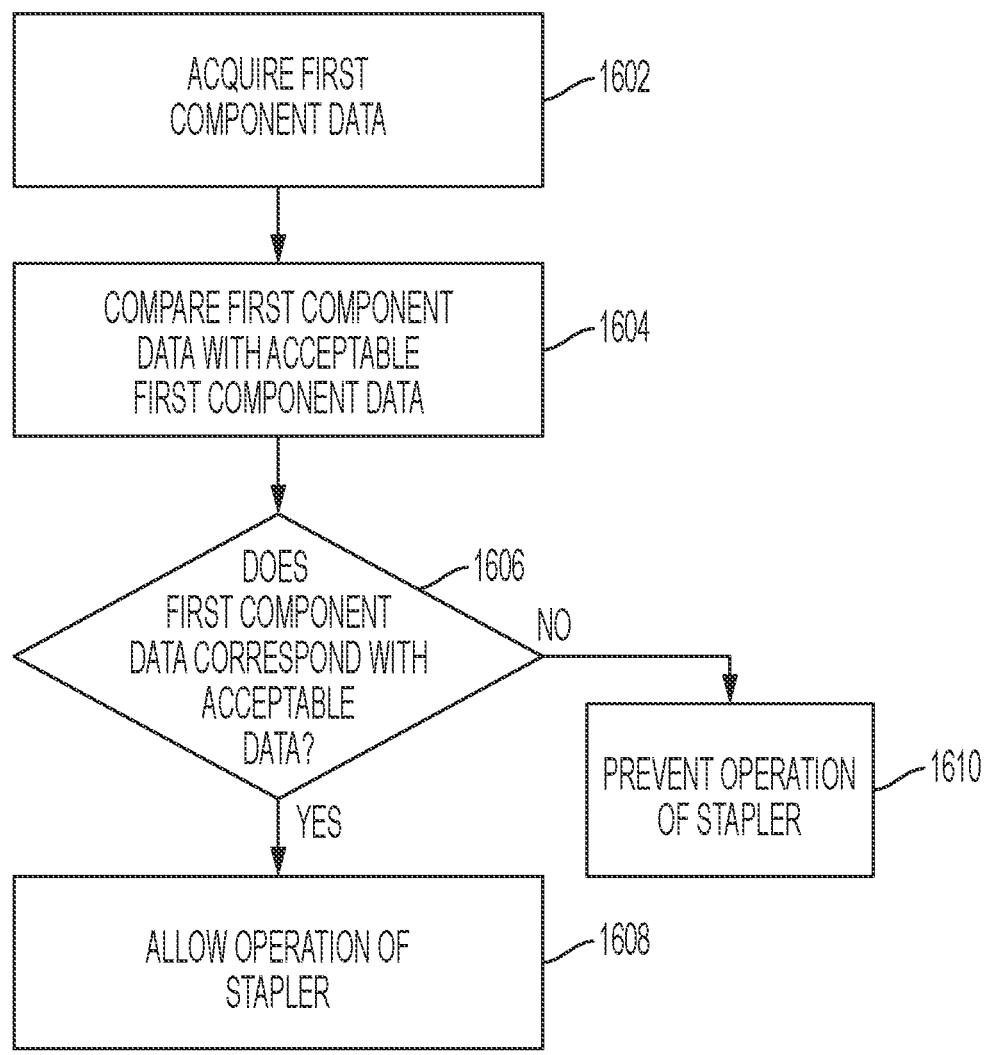
FIG. 25 is a flowing showing one embodiment of a method of establishing compatibility of components.

FIG. 25 illustrates an embodiment of a method of establishing compatibility of components. As shown, the first component data is acquired 1602. As noted herein, the acquisition can occur by, e.g., the first component data being communicated from a data storage component or an image being taken of a first component and the first component data being extracted from the image data.

The first component data is then compared 1604 with acceptable first component data. As noted herein, this comparison can be carried out using a processor, e.g., a processor of a stapler or of an external device. The acceptable first component data can be stored in a memory associated with the processor, and the processor can compare the acquired first component data with the acceptable first component data present in the memory.

Based on this comparison, the processor determines 1606 whether the first component data corresponds with the acceptable first component data. In the situation that the first component data is determined 1606 to correspond with the acceptable first component data, the processor allows 1608 operation of the stapler for tissue clamping and staple and adjunct delivery, such as by writing a flag as a piece of data that indicates that tissue clamping and staple and adjunct delivery operation of the stapler can proceed when needed. The stapler can then be configured to check the status of the flag prior to any tissue clamping and any staple and adjunct delivery. If the first component data is determined 1606 to not correspond with acceptable first component data, then the processor prevents 1610 operation of the stapler, such as by removing an existing flag indicating that the stapler is operational, not writing a flag as a piece of data that indicates that tissue clamping and staple and adjunct delivery operation of the stapler can proceed when needed, or writing a flag as a piece of data that indicates that tissue clamping and staple and adjunct delivery operation of the stapler proceed when needed.

Figure 26:
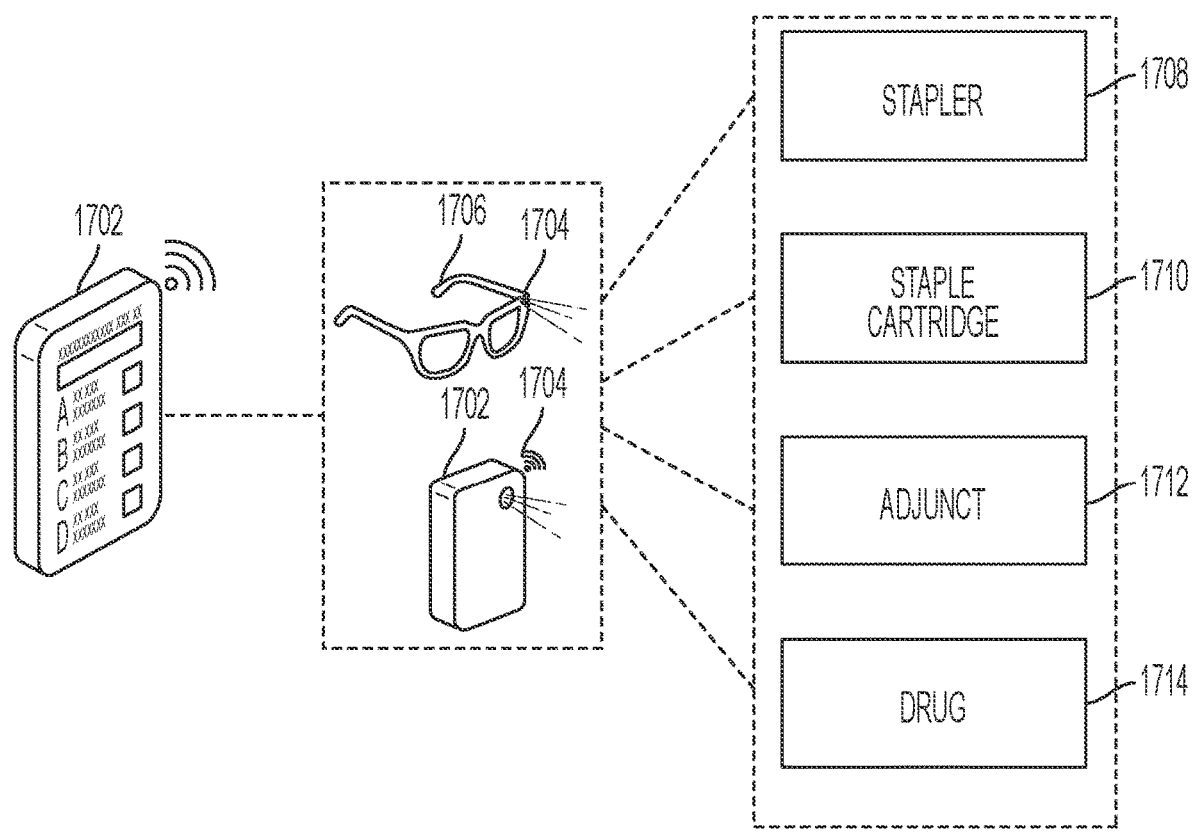
FIG. 26 is a schematic view of part of one embodiment of a compatibility verification system.

FIG. 26 illustrates an embodiment of a compatibility verification system including an external device. The external device in this embodiment is in the form of a smart device 1702 configured to wirelessly interact with other components. The external device 1702 is associated with an image sensor 1704 configured to acquire the first component data in the form of image data. The image sensor 1704 can be present on the smart device 1702 as shown as one alternative in FIG. 26. Alternatively, as shown as another alternative in FIG. 26, the image sensor 1704 can be present on another external device, such as glasses 1706 that can be worn by a user.

The image sensor 1704 can be used to acquire image data of a range of components associated with a stapler and thus confirm whether all the imaged components are appropriate. The imaged components can include any one or more of a stapler 1708, a staple cartridge 1710, an adjunct 1712 releasably coupled to the cartridge 1710, and a drug 1714 releasably retained by the adjunct 1712.

As noted herein, establishing compatibility of components can determine whether the components that used with the stapler are appropriate. The outcome of the assessment can be conveyed to a user via an warning, similar to that discussed above. The warning can be a visual alert on a screen associated with the stapler and/or can be an audio warning. The warning can be different for an indication that the components are compatible and tissue clamping and staple and adjunct delivery can proceed compared to an warning that indicates there is a problem with compatibility and so tissue clamping and staple and adjunct delivery cannot proceed. Alternatively, a warning may only be issued when compatibility is problematic or only when no compatibility issues have been identified.

When a stapler is operated according to stored control parameters, establishing compatibility of components may ensure compatibility with the control parameters. For example, if the stapler has control parameters that indicate a maximum cutting element speed, establishing compatibility of components may ensure that the components are compatible with the cutting element speed and that, e.g., the adjunct will be cut as appropriate and will not unexpectedly tear or otherwise be unintentionally damaged in response to movement of the cutting element therethrough. The control parameters can be stored in a memory of the stapler or of an external device, and the comparison of whether the control parameters are suitable or need to be changed given the first component data or other component data can be carried out by the processor.

In addition to assessing the compatibility of the components, other approaches can be used for ensuring that only compatible devices are utilized. For example, a physical interface between the components can be sized and shaped to limit the physical compatibility to include components that are known to be compatible, such as by a staple cartridge and a jaw of an end effector having complementary mating features. In this way, the number of staple cartridges, and thus adjuncts releasably coupled to the cartridges, that are able to be coupled to the stapler is restricted and thereby reduces the possibility of utilizing non-compatible components.

Devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 issued Feb. 14, 2012 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical adjunct monitoring system, comprising:
   a bioabsorbable adjunct configured to be implanted in a body of a patient;
   a drug configured to be releasably retained by the adjunct and, with the adjunct implanted in the body of the patient and the drug releasably retained by the adjunct, configured to be released from the adjunct into the body of the patient;
   a sensor configured to monitor at least one first exposure condition of at least one of the adjunct and the drug prior to the adjunct being implanted in the body of the patient, the at least one first exposure condition being a condition that affects performance of at least one of the adjunct in the body of the patient and the drug in the body of the patient; and
   a second sensor configured to monitor at least one second exposure condition of the drug from an initial time before the drug is retained by the adjunct to a second time in which the drug is retained by the adjunct.

2. The system of claim 1, further comprising a staple cartridge to which the adjunct is releasably coupled;
   wherein the drug is releasably retained by the adjunct.

3. The system of claim 2, wherein the staple cartridge is a standalone element configured to be removably and replaceably seated in an end effector of a surgical stapler.

4. The system of claim 2, wherein the staple cartridge is seated in an end effector of a surgical stapler.

5. The system of claim 2, wherein the sensor is attached to the staple cartridge.

6. The system of claim 1, wherein the at least one first exposure condition includes at least one of temperature, humidity, time, ultraviolet, oxygen, and light.

7. The system of claim 1, wherein the at least one first exposure condition includes at least one of humidity and oxygen, humidity and oxygen affecting structural resilience of the adjunct.

8. The system of claim 7, wherein the at least one second exposure condition includes at least one of temperature, humidity, time, ultraviolet, oxygen, and light.

9. The system of claim 7, wherein the at least one second exposure condition includes at least time, time affecting an expiration date of the drug.

10. The system of claim 1, wherein the at least one first exposure condition includes at least time, time affecting an expiration date of the drug.

11. The system of claim 10, wherein the at least one second exposure condition includes at least one of temperature, humidity, time, ultraviolet, oxygen, and light.

12. The system of claim 1, wherein the at least one first exposure condition includes at least one of light, ultraviolet, and temperature, light, ultraviolet, and temperature each affecting a viability of the drug.

13. The system of claim 1, further comprising a communications interface configured to communicate data gathered by the sensor to a processor.

14. The system of claim 13, wherein the processor is local to the adjunct and is configured to cause the data to be communicated to a remote cloud server.

15. The system of claim 13, wherein the processor is remote from the adjunct.

16. The system of claim 13, wherein the processor is configured to analyze the data and thereby determine whether at least one exposure condition adversely affected performance of the at least one of the adjunct and the drug.

17. The system of claim 16, wherein the processor is configured to cause a warning to be provided to a user in response to determining that the at least one first exposure condition adversely affected performance of the at least one of the adjunct and the drug.

18. The system of claim 1, further comprising a packaging unit in which the adjunct and the drug are disposed;
    wherein the sensor is attached to the packaging unit.

19. A drug monitoring method, comprising:
    monitoring, by a sensor, at least one first exposure condition of a drug retained in a bioabsorbable adjunct configured to be implanted in a body of a patient after the monitoring;
    transmitting data representative of the at least one first exposure condition to a communications interface in communication with the sensor;
    receiving and transmitting, by the communications interface, the data representative of the at least one first exposure condition to a processor that is in communication with the communications interface;
    monitoring, by a second sensor, at least one second exposure condition of the drug from an initial time before the drug is retained by the adjunct to a second time in which the drug is retained by the adjunct;
    transmitting data representative of the at least one second exposure condition to the communications interface in communication with the second sensor;
    receiving and transmitting, by the communications interface, the data representative of the at least one second exposure condition to the processor; and
    determining, by the processor, viability of the drug based on the received data characterizing the at least one first and second exposure conditions.

20. The method of claim 19, wherein the at least one first exposure condition includes at least one of temperature, humidity, time, ultraviolet, oxygen, and light, and the at least one second exposure condition includes time.

21. The method of claim 20, wherein the at least one second exposure condition includes at least one of temperature, humidity, time, ultraviolet, oxygen, and light, and the at least one first exposure condition includes time.

22. The method of claim 19, wherein the adjunct is releasably coupled to a staple cartridge.

23. The method of claim 22, wherein the staple cartridge is seated in an end effector of a surgical stapler.

24. The method of claim 22, wherein the sensor is attached to the staple cartridge.

25. The method of claim 19, further comprising causing, by the processor, a warning to be provided to a user indicating the determined viability of the drug.

26. The method of claim 19, wherein the sensor is attached to a packaging unit in which the adjunct and the drug are disposed.

* * * * *